(12) United States Patent
Jandrot-Perrus et al.

(10) Patent No.: US 9,045,538 B2
(45) Date of Patent: *Jun. 2, 2015

(54) ANTI-GLYCOPROTEIN VI SCFV FRAGMENT FOR TREATMENT OF THROMBOSIS

(75) Inventors: Martine Jandrot-Perrus, Vanves (FR); Philippe Billiald, Paris (FR); Julien Muzard, Paris (FR)

(73) Assignee: INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 1019 days.

This patent is subject to a terminal disclaimer.

(21) Appl. No.: 12/312,080

(22) PCT Filed: Oct. 26, 2007

(86) PCT No.: PCT/EP2007/061569
§ 371 (c)(1),
(2), (4) Date: Aug. 12, 2009

(87) PCT Pub. No.: WO2008/049928
PCT Pub. Date: May 2, 2008

(65) Prior Publication Data
US 2011/0182899 A1 Jul. 28, 2011

(30) Foreign Application Priority Data
Oct. 26, 2006 (EP) .................................... 06291673

(51) Int. Cl.
| | | |
|---|---|---|
| C12P 21/08 | (2006.01) | |
| A61K 39/00 | (2006.01) | |
| C12N 5/07 | (2010.01) | |
| C12N 5/16 | (2006.01) | |
| C07H 21/04 | (2006.01) | |
| C07K 16/28 | (2006.01) | |
| C07H 21/00 | (2006.01) | |

(52) U.S. Cl.
CPC ................. *C07K 16/28* (2013.01); *A61K 39/00* (2013.01); *C07H 21/00* (2013.01); *A61K 2039/505* (2013.01); *C07K 16/2803* (2013.01); *C07K 2317/24* (2013.01); *C07K 2317/622* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,585,089 A | 12/1996 | Queen et al. | |
| 5,859,205 A | 1/1999 | Adair et al. | |
| 7,611,707 B2 * | 11/2009 | Tandon et al. | 424/143.1 |
| 2003/0017149 A1 * | 1/2003 | Hoeffler et al. | 424/130.1 |

FOREIGN PATENT DOCUMENTS

| | | |
|---|---|---|
| EP | 0 173 494 A2 | 3/1986 |
| EP | 1 224 942 A1 | 7/2002 |
| EP | 1 228 768 A1 | 8/2002 |
| EP | 1 522 590 A1 | 4/2005 |
| EP | 1 538 165 A1 | 6/2005 |
| EP | 1 297 172 B1 | 11/2005 |
| WO | WO 87/02671 A1 | 5/1987 |
| WO | WO 98/45322 A2 | 10/1998 |
| WO | WO 01/00810 A1 | 1/2001 |
| WO | WO 03/008454 A2 | 1/2003 |
| WO | WO 2005/111083 A2 | 11/2005 |

OTHER PUBLICATIONS

Cullen et al., HEP 2005, 170:3-70.*
Muzard et al., Human Antibodies, 2006, 15(1-2): pp. 24.*
Chothia et al., "Canonical Structures for the Hypervariable Regions of Immunoglobulins," *J. Mol. Biol.*, vol. 196, pp. 901-917, 1987.
Tsurushita et al., "Design of humanized antibodies: From anti-Tac to Zenapax," *Methods*, vol. 36, pp. 69-83, 2005.
Fontayne et al., "Rational humanization of the powerful antithrombotic anti-GPIbα antibody: 6B4," *Thromb Haemost*, vol. 96, pp. 671-684, 2006.
Lazar et al., "A molecular immunology approach to antibody humanization and functional optimization," *Molecular Immunology*, vol. 44, pp. 1986-1998, 2007.
Jones et al., "Replacing the complementarity-determining regions in a human antibody with those from a mouse," *Nature*, vol. 321, pp. 522-525, May 29, 1986.
Verhoeyen et al., "Reshaping Human Antibodies: Grafting an Antilysozyme Activity," *Science*, vol. 239, pp. 1534-1536, Mar. 25, 1988.
Caldas et al., "Humanization of the anti-CD18 antibody 6.7: an unexpected effect of a framework residue in binding to antigen," *Molecular Immunology*, vol. 39, pp. 941-952, 2003.
Gonzales et al., "SDR grafting of a murine antibody using multiple human germline templates to minimize its immunogenicity," *Molecular Immunology*, vol. 41, pp. 863-872, 2004.
Riechmann et al., "Reshaping human antibodies for therapy," *Nature*, vol. 332, pp. 323-327, Mar. 24, 1988.
Winter et al., "Man-made antibodies," *Nature*, vol. 349, pp. 293-299, Jan. 24, 1991.
Ewert et al., "Stability improvement of antibodies for extracellular and intracellular applications: CDR grafting to stable frameworks and structure-based framework engineering," *Methods*, vol. 34, pp. 184-199, 2004.
Hamilton et al., "Production of Complex Human Glycoproteins in Yeast," *Science*, vol. 301, pp. 1244-1246, Aug. 29, 2003.

(Continued)

*Primary Examiner* — Hong Sang
(74) *Attorney, Agent, or Firm* — McAndrews Held & Malloy, Ltd.

(57) ABSTRACT

The present invention relates to a single chain variable fragment (scFv 9O12.2) directed against human glycoprotein VI, constituted of the VH and VL domains of 9 O12.2.2 monoclonal antibody linked via a $(Gly_4Ser)_3$ peptide and followed by a "c-myc" flag, represented by SEQ ID NO:1. The invention also concerns functional variants of said scFv 9O12.2 fragment with identical heavy and light chains complementary determining regions 1, 2 and 3, and preferably humanized functional variants such as the humanized scFv fragments represented by SEQ ID NO:28 or SEQ ID NO:47. The invention also relates to nucleic acids encoding such a scFv fragment, expression vectors and host cells to produce such a scFv fragment, as well as therapeutic uses of such a scFv fragment.

10 Claims, 20 Drawing Sheets

(56) References Cited

OTHER PUBLICATIONS

Wildt et al., "The Humanization of N-Glycosylation Pathways in Yeast," *Nature Reviews Microbiology*, vol. 3, pp. 119-128, Feb. 2005.

Ward et al., "Binding activities of a repertoire of single immunoglobulin variable domains secreted from *Escherichia coli*," *Nature*, vol. 341, pp. 544-546, Oct. 12, 1989.

Hemker et al., "The Thrombogram: Monitoring Thrombin Generation in Platelet Rich Plasma," *Thromb. Haemost.*, vol. 83, pp. 589-591, 2000.

Lecut et al., "Principal Role of Glycoprotein VI in α2β1 and αIIbβ3 Activation During collagen-Induced Thrombus Formation," *Arterioscler. Thromb, Vasc. Biol.*, pp. 1727-1733, Sep. 2004.

International Search Report issued on May 2, 2008 for application No. PCT/EP2007/061569.

European Search Report issued on Mar. 23, 2007 for application No. EP 06 29 1673.

Massberg et al., "Soluble glycoprotein VI dimmer inhibits platelet adhesion and aggregation to the injured vessel wall in vivo," *FASEB Journal*, published online Dec. 4, 2003, 10.1096/fj.03-0464.fje.

Gruner et al., "Relative antithrombotic effect of soluble GPVI dimmer compared with anti-GPVI antibodies in mice," *Blood*, vol. 105, No. 4, pp. 1492-1499 (Feb. 15, 2005).

Lecut et al., "Human platelet glycoprotein VI function is antagonized by monoclonal antibody-derived Fab fragments," *Journal of Thrombosis and Haemostasis*, vol. 1, pp. 2653-2662 (2003).

Nieswandt et al., "Long-term Antithrombotic Protection by In Vivo Depletion of Platelet Glycoprotein VI in Mice," *J. Exp. Med.*, vol. 193, No. 4, pp. 459-469 (Feb. 19, 2001).

Qian et al., "Anti GPVI human antibodies neutralizing collagen-induced platelet aggregation isolated from a combinatorial phage display library," *Human Antibodies*, vol. 11, No. 3, pp. 97-105 (2002).

Siljander et al., "Platelet receptor interplay regulates collagen-induced thrombus formation in flowing human blood," *Blood*, vol. 103, No. 4, pp. 1333-1341 (Feb. 15, 2004).

Matsumoto et al., "Highly potent anti-human GPVI monoclonal antibodies derived from GPVI knockout mouse immunization," *Thrombosis Research*, 11 pages (2006).

Juste et al., "Cloning of the antibody κ light chain V-gene from murine hybridomas by bypassing the aberrant MOPC21-derived transcript," *Analytical Biochemistry*, vol. 349, pp. 159-161 (2006).

Lecut et al., "Fibrillar type I collagens enhance platelet-dependent thrombin generation via glycoprotein VI with direct support of α2β1 but not αIIbβ3 integrin," *Thromb. Haemost.*, pp. 107-114 (2005).

Sugiyama et al, "A Novel Platelet Aggregating Factor Found in a Patient with Defective Collagen-Induced Platelet Aggregation and Autoimmune Thrombocytopenia," *Blood*, vol. 69, No. 6, pp. 1712-1720 (1987).

Lecut et al., "Identification of Residues within Human Glycoprotein VI Involved in the Binding to Collagen," *Journal of Biological Chemistry*, vol. 279, No. 50, pp. 52293-52299 (2004).

Smethurst et al., "Identification of the primary collagen-binding surface on human glycoprotein VI by site-directed mutagenesis and by a blocking phage antibody," *Blood*, vol. 103, No. 3, pp. 903-911 (Feb. 1, 2004).

\* cited by examiner

```
1                  21                 41                 61                 81
|                  |                  |                  |                  |
CAG GTC CAG CPGCAGGAGTCAGGGGCTGAGCTGGTGAAGCCTGGGCTTCAGTGAAGATGTCCTGCAAGGCTTCTGGCTACACATTTACC
 Q   V   Q   L   Q   E   S   G   A   E   L   V   K   P   G   A   S   V   K   M   S   C   K   A   S   G   Y   T   F   T
         ▲
         PstI (U)

101                121                141                161
              CDR H1 |             |                  |                  |         CDR H2
         AGTTACAATATGCACTGGGTAAAGCAGACACCTGGACAGGGCCTGGAATGGATTGGAGGTATTTATCCAGGAAATGGTGACACTTCCTTC
          S   Y   N   M   H   W   V   K   Q   T   P   G   Q   G   L   E   W   I   G   G   I   Y   P   G   N   G   D   T   S   F 181                201                221                241                261
         |                  |                  |                  |                  |
         AATCAGAAGTTCAAAGGCAAGGCCACATTGACAGCTGACAAATCCTCCAGGACAGCCTACATGCAGCTCAGCAGCCTGACATCTGAGGAC
          N   Q   K   F   K   G   K   A   T   L   T   A   D   K   S   S   R   T   A   Y   M   Q   L   S   S   L   T   S   E   D 281                301                321                341
                   |                  |        CDR H3    |                  |
         TCTGCGGTCTATTACTGTGCAAGAGGAACGGTAGTAGGCGACTGGTACTTCGATGTCTGGGGCGCAGGACCACTCTCACAGTCTCCTCA
          S   A   V   Y   Y   C   A   R   G   T   V   V   G   D   W   Y   F   D   V   W   G   A   G   T   T   L   T   V   S   S 361                381                401                421                441
              |                  |                  |                  |                  |
         GGCGGAGGCGGATCCGGTGGTGGCGGATCTGGAGGTGGCGGAAGCGATGTTTTGATGACCCAAACTCCACTCTCCCTGCCTGTCAGTCTT
          G   G   G   G   S   G   G   G   G   S   G   G   G   G   S   D   V   L   M   T   Q   T   P   L   S   L   P   V   S   L 461                481                501                521
                   |                  |            CDR L1 |                  |
         GGAGATCAAGCCCTCATCTCTTGCAGGTCTAGTCAGAGCCTTGAAAACAGTAATGGAAACACCTATTTGAACTGGTACCTCCAGAAACCA
          G   D   Q   A   S   I   S   C   R   S   S   Q   S   L   E   N   S   N   G   N   T   Y   L   N   W   Y   L   Q   K   P 541                561                581                601                621
         |                  |         CDR L2   |                  |                  |
         GGCCAGTCTCCACAGCTCCTGATCTACAGGGTTTCAACCGATTTTCTGGGGTCCTAGACAGTTCAGTGGTAGTGGATCAGGGACAGAT
          G   Q   S   P   Q   L   L   I   Y   R   V   S   N   R   F   S   G   V   L   D   R   F   S   G   S   G   S   G   T   D 641                661                681                701
              |                  |                  |           CDR L3 |
         TTCACACTGAAAATCAGCAGAGTGGAGGCTGAGGATTTGGGAGTTTATTTCTGCCTCCAACTTACACATGTCCCGTGGACGTTCGGTGGA
          F   T   L   K   I   S   R   V   E   A   E   D   L   G   V   Y   F   C   L   Q   L   T   H   V   P   W   T   F   G   G 721                741                761                781                801
         |                  |        spacer    |         c-myc    |                  |
         GGCACCAAGCTGGAGATCAAACGCTCGAGGGTCATCCGTCTCCTCAGAACAAAAACTCATCTCAGAAGAGGATCTGAATTAATAA
          G   T   K   L   E   I   K   R   S   R   V   I   R   L   L   R   T   K   T   H   L   R   R   G   S   E   L   I   N   *
                                      ▲
                                      XhoI (U)
```

Figure 2

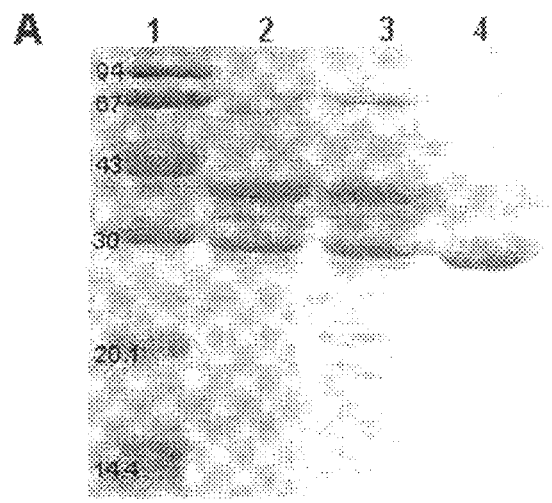
Figure 5

A Humanized 9012.2 VH (1)

>CAGGTGCAGCTGCAGGAGAGCGGCGCGGAAGTGAAAAAACCGGGCGCGAGCGTGAAAGTGAGCTGTAAAGCGAGCGG
CTATAGCTTTACCAGCTATAATATGCATTGGGTGCGTCAGGCGCCGGGCCAGCGTCTAGAATGGATGGGCGGCATTTA
TCCGGGCAATGGCGATACCAGCTTTAATCAGAAATTTAAAGGCAAAGCGACCCTGACCGCCGATAAAAGCAGCCGTAC
CGCGTATATGGGCCTGAGCAGCCTGCGCCCGGAAGACACCGCCGTGTATTATTGTGCGCGTGGCACCGTGGTGGGCGA
TTGGTATTTTGATGTGTGGGGCCAGGGCACCCTGGTGACCGTGAGCAGC (SEQ ID NO:31)

```
Q  V  Q  L  Q  E  S  G  A  E  V  K  K  P  G  A  S  V  K  V  S  C  K  A  S  G
Y  S  F  T  S  Y  N  M  H  W  V  R  Q  A  P  G  Q  R  L  E  W  M  G  G  I  Y
P  G  N  G  D  T  S  F  N  Q  K  F  K  G  K  A  T  L  T  A  D  K  S  S  R  T
A  Y  M  G  L  S  S  L  R  P  E  D  T  A  V  Y  Y  C  A  R  G  T  V  V  G  D
W  Y  F  D  V  W  G  Q  G  T  L  V  T  V  S  S    (SEQ ID NO :26)
```

Figure 14A

B Humanized 9012.2 VL

>GATGTGCTGATGACCCAGAGCCCGAGCAGCCTGAGCGCCAGCGTGGGCGATCGTGTGAACATTGCCTGCCGTAGCAG
CCAGAGCCTGGAAATGAGCAACGGCAACACCTATCTGAACTGGTATCTCCAGAAACCGGGCAAAGCGCCGCGGCTGCT
GATTTATCGTGTGAGCAACCGTTTTAGCGGCGTGCCGAGCCGCTTTAGCGGCTCCGGAAGCGGCACCGATTTTACCCT
GACCATTAGCAGCCTCCAGCCGGAAGATTTTGCCATCTATTATTGCCTCCAGCTGACCCATGTGCCGTGGACCTTTGG
TGGCGGCACCAAAGTGGAAATCAAACGCTCGAGAGTTACCGTTAGCAGCGAACAGAAACTGATTAGCGAAGAAGATCT
GAATTAATAATAAG (SEQ ID NO :32)

```
D  V  L  M  T  Q  S  P  S  S  L  S  A  S  V  G  D  R  V  N  I  A  C  R  S  S
Q  S  L  E  N  S  N  G  N  T  Y  L  N  W  Y  L  Q  K  P  G  K  A  P  R  L  L
I  Y  R  V  S  N  R  F  S  G  V  P  S  R  F  S  G  S  G  T  D  F  T  L
T  I  S  S  L  Q  P  E  D  F  A  I  Y  Y  C  L  Q  L  T  H  V  P  W  T  F  G  G
G  T  K  V  E  I  K  R  S  R  V  T  V  S  S  E  Q  K  L  I  S  E  E  D  L  N
-  -  -    (SEQ ID NO:27)
```

Figure 14B

C Humanized 9012.2 scFv fragment

>CAGGTCCAGCTGCAGGAGAGCGGCGCGGAAGTGAAAAAACCGGGCGCGAGCGTGAAAGTGAGCTGTAAAGCGAGCGG
CTATAGCTTTACCAGCTATAATATGCATTGGGTGCGTCAGGCGCCGGGCCAGGGTCTAGAATGGATGGGCGGCATTTA
TCCGGGCAATGGCGATACCAGCTTTAATCAGAAATTTAAAGGCAAAGCGACCCTGACCGCCGATAAAAGCAGTCGTAC
CGCGTATATGGGCCTGAGCAGCCTGCGCCCGGAAGACACCGCCGTGTATTATTGTGCGCGTGGCACCGTCGTGGGCGA
TTGGTATTTTGATGTGTGGGGCCAGGGCACCCTGGTGACCGTGAGCAGCGGCGGAGCCGGATCCGGTGGTGGCGGATC
TGGAGGTGGCGGAAGCGATGTGCTGATGACCCAGAGCCCGAGCAGCCTGAGCGCCAGCGTGGGCGATCGTGTGAACAT
TGCCTGCCGTAGCAGCCAGAGCCTGGAAAATGAGCAACGGCAACACCTATCTGAACTGGTATCTCCAGAAACCGGGCAA
AGCGCCGCGCCTGCTGATTTATCGTGTGAGCAACCGTTTTAGCGGCGTGCCGAGCCGCTTTAGCGGCTCGGAAGCGG
CACCGATTTTACCCTGACCAGTTAGCAGCCTCCAGCCGGAAGATTTTGCCATCTATTATTGCCTCCAGCTGACCCATGT
GCCGTGGACCTTTGGTGGCGGCACCAAAGTGGAAATCAAACGCTCGAGAGTTACCGTTAGCAGCGAACAGAAACTGAT
TAGCGAAGAAGATCTGAATTAATAATAAG (SEQ ID NO :30)

```
Q V Q L Q E S G A E V K K P G A S V K V S C K A S G
Y S F T S Y N M H W V R Q A P G Q K L E W M G G I Y
P G N G D T S F N Q K F K G K A T L T A D K S S R T
A Y M G L S S L R P E D T A V Y Y C A R G T V V G D
W Y F D V W G Q G T L V T V S S G G G G S G G G G S
G G G G S D V L M T Q S P S S L S A S V G D R V N I
A C R S S Q S L E N S N G N T Y L N W Y L Q K P G K
A P R L L I Y R V S N R F S G V P S R F S G S G S G
T D F T L T I S S L Q P E D F A I Y Y C L Q L T H V
P W T F G G G T K V E I K R S R V T V S S E Q K L I
S E E D L N - - - (SEQ ID NO:28)
```

Figure 14C

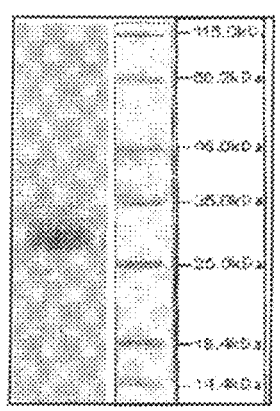

A
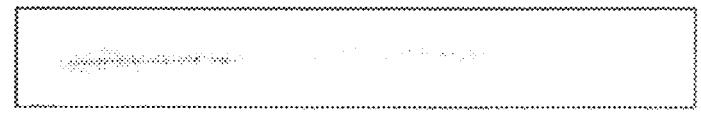
mscFv   hscFv (2)   control
B
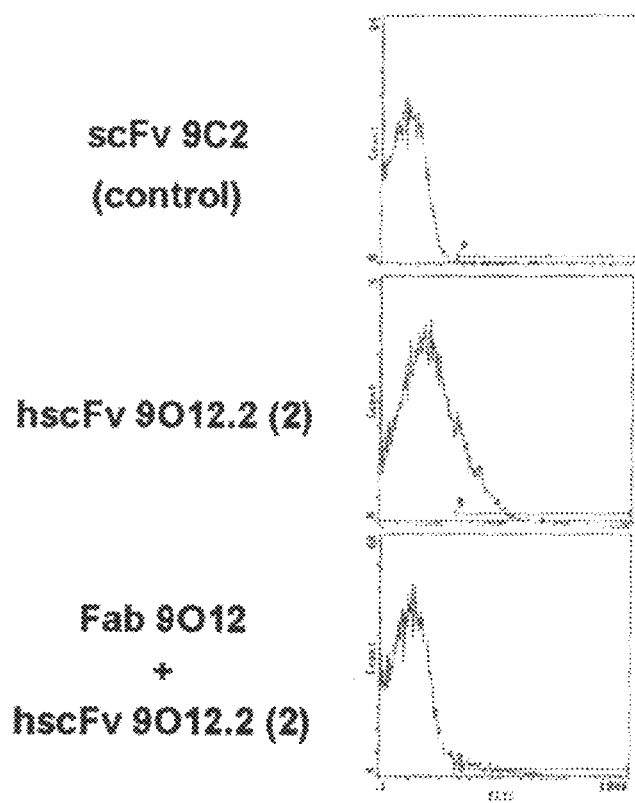
scFv 9C2 (control)
hscFv 9O12.2 (2)
Fab 9O12 + hscFv 9O12.2 (2)
Figure 20

```
                        SEQUENCE LISTING

<160> NUMBER OF SEQ ID NOS: 53

<210> SEQ ID NO 1
<211> LENGTH: 266
<212> TYPE: PRT
<213> ORGANISM: Artificial sequence
<220> FEATURE:
<223> OTHER INFORMATION: Murine 9012.2 scFv fragment complete amino acid
      sequence

<400> SEQUENCE: 1

Gln Val Gln Leu Gln Glu Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Gly Ile Tyr Pro Gly Asn Gly Asp Thr Ser Phe Asn Gln Lys Phe
    50                  55                  60

Lys Gly Lys Ala Thr Leu Thr Ala Asp Lys Ser Ser Arg Thr Ala Tyr
65                  70                  75                  80

Met Gln Leu Ser Ser Leu Thr Ser Glu Asp Ser Ala Val Tyr Tyr Cys
```

```
            85                  90                  95
Ala Arg Gly Thr Val Gly Asp Trp Tyr Phe Asp Val Trp Gly Ala
            100                 105                 110

Gly Thr Thr Leu Thr Val Ser Ser Gly Gly Gly Ser Gly Gly Gly
            115                 120                 125

Gly Ser Gly Gly Gly Ser Asp Val Leu Met Thr Gln Thr Pro Leu
130                 135                 140

Ser Leu Pro Val Ser Leu Gly Asp Gln Ala Ser Ile Ser Cys Arg Ser
145                 150                 155                 160

Ser Gln Ser Leu Glu Asn Ser Asn Gly Asn Thr Tyr Leu Asn Trp Tyr
            165                 170                 175

Leu Gln Lys Pro Gly Gln Ser Pro Gln Leu Leu Ile Tyr Arg Val Ser
            180                 185                 190

Asn Arg Phe Ser Gly Val Leu Asp Arg Phe Ser Gly Ser Gly Ser Gly
            195                 200                 205

Thr Asp Phe Thr Leu Lys Ile Ser Arg Val Glu Ala Glu Asp Leu Gly
210                 215                 220

Val Tyr Phe Cys Leu Gln Leu Thr His Val Pro Trp Thr Phe Gly Gly
225                 230                 235                 240

Gly Thr Lys Leu Glu Ile Lys Arg Ser Arg Val Thr Val Ser Ser Glu
            245                 250                 255

Gln Lys Leu Ile Ser Glu Glu Asp Leu Asn
            260                 265

<210> SEQ ID NO 2
<211> LENGTH: 10
<212> TYPE: PRT
<213> ORGANISM: Artificial sequence
<220> FEATURE:
<223> OTHER INFORMATION: Murine 9012.2 scFv fragment VH domain CDR1

<400> SEQUENCE: 2

Gly Tyr Thr Phe Thr Ser Tyr Asn Met His
1               5                   10

<210> SEQ ID NO 3
<211> LENGTH: 17
<212> TYPE: PRT
<213> ORGANISM: Artificial sequence
<220> FEATURE:
<223> OTHER INFORMATION: Murine 9012.2 scFv fragment VH domain CDR2

<400> SEQUENCE: 3

Gly Ile Tyr Pro Gly Asn Gly Asp Thr Ser Phe Asn Gln Lys Phe Lys
1               5                   10                  15
Gly

<210> SEQ ID NO 4
<211> LENGTH: 11
<212> TYPE: PRT
<213> ORGANISM: Artificial sequence
<220> FEATURE:
<223> OTHER INFORMATION: Murine 9012.2 scFv fragment VH domain CDR3

<400> SEQUENCE: 4

Gly Thr Val Val Gly Asp Trp Tyr Phe Asp Val
1               5                   10

<210> SEQ ID NO 5
<211> LENGTH: 16
```

```
<212> TYPE: PRT
<213> ORGANISM: Artificial sequence
<220> FEATURE:
<223> OTHER INFORMATION: Murine 9012.2 scFv fragment VL domain CDR1

<400> SEQUENCE: 5

Arg Ser Ser Gln Ser Leu Glu Asn Ser Asn Gly Asn Thr Tyr Leu Asn
1               5                   10                  15

<210> SEQ ID NO 6
<211> LENGTH: 7
<212> TYPE: PRT
<213> ORGANISM: Artificial sequence
<220> FEATURE:
<223> OTHER INFORMATION: Murine 9012.2 scFv fragment VL domain CDR2

<400> SEQUENCE: 6

Arg Val Ser Asn Arg Phe Ser
1               5

<210> SEQ ID NO 7
<211> LENGTH: 9
<212> TYPE: PRT
<213> ORGANISM: Artificial sequence
<220> FEATURE:
<223> OTHER INFORMATION: Murine 9012.2 scFv fragment VL domain CDR3

<400> SEQUENCE: 7

Leu Gln Leu Thr His Val Pro Trp Thr
1               5

<210> SEQ ID NO 8
<211> LENGTH: 15
<212> TYPE: PRT
<213> ORGANISM: Artificial sequence
<220> FEATURE:
<223> OTHER INFORMATION: Suitable peptide linker

<400> SEQUENCE: 8

Gly Gly Gly Gly Ser Gly Gly Gly Ser Gly Gly Gly Gly Ser
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Suitable peptide linker

<400> SEQUENCE: 9

Gly Gly Gly Gly Ile Ala Pro Ser Met Val Gly Gly Gly Ser
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: Suitable peptide linker

<400> SEQUENCE: 10

Gly Gly Gly Gly Lys Val Glu Gly Ala Gly Gly Gly Gly Ser
1               5                   10                  15

<210> SEQ ID NO 11
<211> LENGTH: 15
<212> TYPE: PRT
```

```
<213> ORGANISM: Artificial sequence
<220> FEATURE:
<223> OTHER INFORMATION: Suitable peptide linker

<400> SEQUENCE: 11

Gly Gly Gly Gly Ser Met Lys Ser His Asp Gly Gly Gly Gly Ser
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: Suitable peptide linker

<400> SEQUENCE: 12

Gly Gly Gly Gly Asn Leu Ile Thr Ile Val Gly Gly Gly Gly Ser
1               5                   10                  15

<210> SEQ ID NO 13
<211> LENGTH: 14
<212> TYPE: PRT
<213> ORGANISM: Artificial sequence
<220> FEATURE:
<223> OTHER INFORMATION: Suitable peptide linker

<400> SEQUENCE: 13

Gly Gly Gly Gly Val Val Pro Ser Leu Gly Gly Gly Gly Ser
1               5                   10

<210> SEQ ID NO 14
<211> LENGTH: 12
<212> TYPE: PRT
<213> ORGANISM: Artificial sequence
<220> FEATURE:
<223> OTHER INFORMATION: Suitable peptide linker

<400> SEQUENCE: 14

Gly Gly Glu Lys Ser Ile Pro Gly Gly Gly Gly Ser
1               5                   10

<210> SEQ ID NO 15
<211> LENGTH: 18
<212> TYPE: PRT
<213> ORGANISM: Artificial sequence
<220> FEATURE:
<223> OTHER INFORMATION: Suitable peptide linker

<400> SEQUENCE: 15

Gly Ser Thr Ser Gly Ser Gly Lys Ser Ser Glu Gly Ser Gly Ser Thr
1               5                   10                  15

Lys Gly

<210> SEQ ID NO 16
<211> LENGTH: 6
<212> TYPE: PRT
<213> ORGANISM: Artificial sequence
<220> FEATURE:
<223> OTHER INFORMATION: Suitable peptide tag

<400> SEQUENCE: 16

His His His His His His
1               5

<210> SEQ ID NO 17
<211> LENGTH: 11
```

```
<212> TYPE: PRT
<213> ORGANISM: Artificial sequence
<220> FEATURE:
<223> OTHER INFORMATION: Suitable peptide tag

<400> SEQUENCE: 17

Glu Gln Lys Leu Ile Ser Glu Glu Asp Leu Asn
1               5                   10

<210> SEQ ID NO 18
<211> LENGTH: 9
<212> TYPE: PRT
<213> ORGANISM: Artificial sequence
<220> FEATURE:
<223> OTHER INFORMATION: Suitable peptide tag

<400> SEQUENCE: 18

Tyr Pro Tyr Asp Val Pro Asp Tyr Ala
1               5

<210> SEQ ID NO 19
<211> LENGTH: 8
<212> TYPE: PRT
<213> ORGANISM: Artificial sequence
<220> FEATURE:
<223> OTHER INFORMATION: Suitable peptide tag

<400> SEQUENCE: 19

Asp Tyr Lys Asp Asp Asp Asp Lys
1               5

<210> SEQ ID NO 20
<211> LENGTH: 12
<212> TYPE: PRT
<213> ORGANISM: Artificial sequence
<220> FEATURE:
<223> OTHER INFORMATION: Suitable peptide tag

<400> SEQUENCE: 20

Glu Asp Gln Val Asp Pro Arg Leu Ile Asp Gly Lys
1               5                   10

<210> SEQ ID NO 21
<211> LENGTH: 12
<212> TYPE: PRT
<213> ORGANISM: Artificial sequence
<220> FEATURE:
<223> OTHER INFORMATION: Suitable peptide tag

<400> SEQUENCE: 21

Glu Glu Thr Ala Arg Phe Gln Pro Gly Tyr Arg Ser
1               5                   10

<210> SEQ ID NO 22
<211> LENGTH: 14
<212> TYPE: PRT
<213> ORGANISM: Artificial sequence
<220> FEATURE:
<223> OTHER INFORMATION: Suitable peptide tag

<400> SEQUENCE: 22

Gly Lys Pro Ile Pro Asn Pro Leu Leu Gly Leu Asp Ser Thr
1               5                   10

<210> SEQ ID NO 23
<211> LENGTH: 11
<212> TYPE: PRT
```

<213> ORGANISM: Artificial sequence
<220> FEATURE:
<223> OTHER INFORMATION: Suitable peptide tag

<400> SEQUENCE: 23

Tyr Thr Asp Ile Glu Met Asn Arg Leu Gly Lys
1               5                   10

<210> SEQ ID NO 24
<211> LENGTH: 8
<212> TYPE: PRT
<213> ORGANISM: Artificial sequence
<220> FEATURE:
<223> OTHER INFORMATION: Suitable peptide tag

<400> SEQUENCE: 24

Asp Leu Tyr Asp Asp Asp Asp Lys
1               5

<210> SEQ ID NO 25
<211> LENGTH: 8
<212> TYPE: PRT
<213> ORGANISM: Artificial sequence
<220> FEATURE:
<223> OTHER INFORMATION: Suitable peptide spacer

<400> SEQUENCE: 25

Arg Ser Arg Val Thr Val Ser Ser
1               5

<210> SEQ ID NO 26
<211> LENGTH: 120
<212> TYPE: PRT
<213> ORGANISM: Artificial sequence
<220> FEATURE:
<223> OTHER INFORMATION: First humanized 9012.2 scFv fragment VH amino
     acid sequence

<400> SEQUENCE: 26

Gln Val Gln Leu Gln Glu Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Asn Met His Trp Val Arg Gln Ala Pro Gly Gln Arg Leu Glu Trp Met
            35                  40                  45

Gly Gly Ile Tyr Pro Gly Asn Gly Asp Thr Ser Phe Asn Gln Lys Phe
        50                  55                  60

Lys Gly Lys Ala Thr Leu Thr Ala Asp Lys Ser Ser Arg Thr Ala Tyr
65                  70                  75                  80

Met Gly Leu Ser Ser Leu Arg Pro Glu Asp Thr Ala Val Tyr Tyr Cys
                85                  90                  95

Ala Arg Gly Thr Val Val Gly Asp Trp Tyr Phe Asp Val Trp Gly Gln
                100                 105                 110

Gly Thr Leu Val Thr Val Ser Ser
            115                 120

<210> SEQ ID NO 27
<211> LENGTH: 131
<212> TYPE: PRT
<213> ORGANISM: Artificial sequence
<220> FEATURE:
<223> OTHER INFORMATION: First humanized 9012.2 scFv fragment VL amino
     acid sequence

<400> SEQUENCE: 27

```
Asp Val Leu Met Thr Gln Ser Pro Ser Ser Leu Ser Ala Ser Val Gly
1               5                   10                  15

Asp Arg Val Asn Ile Ala Cys Arg Ser Ser Gln Ser Leu Glu Asn Ser
            20                  25                  30

Asn Gly Asn Thr Tyr Leu Asn Trp Tyr Leu Gln Lys Pro Gly Lys Ala
        35                  40                  45

Pro Arg Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Ile Tyr Tyr Cys Leu Gln Leu
                85                  90                  95

Thr His Val Pro Trp Thr Phe Gly Gly Gly Thr Lys Val Glu Ile Lys
            100                 105                 110

Arg Ser Arg Val Thr Val Ser Ser Glu Gln Lys Leu Ile Ser Glu Glu
            115                 120                 125

Asp Leu Asn
    130
```

<210> SEQ ID NO 28
<211> LENGTH: 266
<212> TYPE: PRT
<213> ORGANISM: Artificial sequence
<220> FEATURE:
<223> OTHER INFORMATION: First humanized 9012.2 scFv fragment complete amino acid sequence

<400> SEQUENCE: 28

```
Gln Val Gln Leu Gln Glu Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Asn Met His Trp Val Arg Gln Ala Pro Gly Gln Arg Leu Glu Trp Met
        35                  40                  45

Gly Gly Ile Tyr Pro Gly Asn Gly Asp Thr Ser Phe Asn Gln Lys Phe
    50                  55                  60

Lys Gly Lys Ala Thr Leu Thr Ala Asp Lys Ser Ser Arg Thr Ala Tyr
65                  70                  75                  80

Met Gly Leu Ser Ser Leu Arg Pro Glu Asp Thr Ala Val Tyr Tyr Cys
                85                  90                  95

Ala Arg Gly Thr Val Val Gly Asp Trp Tyr Phe Asp Val Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Asp Val Leu Met Thr Gln Ser Pro Ser
130                 135                 140

Ser Leu Ser Ala Ser Val Gly Asp Arg Val Asn Ile Ala Cys Arg Ser
145                 150                 155                 160

Ser Gln Ser Leu Glu Asn Ser Asn Gly Asn Thr Tyr Leu Asn Trp Tyr
                165                 170                 175

Leu Gln Lys Pro Gly Lys Ala Pro Arg Leu Leu Ile Tyr Arg Val Ser
            180                 185                 190

Asn Arg Phe Ser Gly Val Pro Ser Arg Phe Ser Gly Ser Gly Ser Gly
        195                 200                 205
```

```
Thr Asp Phe Thr Leu Thr Ile Ser Ser Leu Gln Pro Glu Asp Phe Ala
    210                 215                 220

Ile Tyr Tyr Cys Leu Gln Leu Thr His Val Pro Trp Thr Phe Gly Gly
225                 230                 235                 240

Gly Thr Lys Val Glu Ile Lys Arg Ser Arg Val Thr Val Ser Ser Glu
                245                 250                 255

Gln Lys Leu Ile Ser Glu Glu Asp Leu Asn
            260                 265

<210> SEQ ID NO 29
<211> LENGTH: 804
<212> TYPE: DNA
<213> ORGANISM: Artificial sequence
<220> FEATURE:
<223> OTHER INFORMATION: First humanized 9012.2 scFv fragment VH
      nucleotide sequence

<400> SEQUENCE: 29
caggtgcagc tgcaggagtc aggggctgag ctggtgaagc ctggggcttc agtgaagatg      60
tcctgcaagg cttctggcta cacatttacc agttacaata tgcactgggt aaagcagaca     120
cctggacagg gcctggaatg gattggaggt atttatccag aaaatggtga cacttccttc     180
aatcagaagt tcaaaggcaa ggccacattg acagctgaca atcctccag acagcctac       240 atgcagctca gcagcctgac atctgaggac tctgcggtct attactgtgc aagaggaacg     300
gtagtaggcg actggtactt cgatgtctgg ggcgcaggga ccactctcac agtctcctca     360 ggcgaggcg atccggtgg tggcggatct ggaggtggcg aagcgatgt tttgatgacc        420 caaactccac tctccctgcc tgtcagtctt ggagatcaag cctccatctc ttgcaggtct    480
agtcagagcc ttgaaaacag taatggaaac acctatttga actggtacct ccagaaacca     540
ggccagtctc cacagctcct gatctacagg gtttccaacc gattttctgg ggtcctagac     600
aggttcagtg gtagtggatc agggacagat ttcacactga aaatcagcag agtggaggct     660
gaggatttgg gagtttattt ctgcctccaa cttacacatg tcccgtggac gttcggtgga     720
ggcaccaagc tggagatcaa acgctcgagg gtcaccgtct cctcagaaca aaaactcatc    780
tcagaagagg atctgaatta taa                                            804

<210> SEQ ID NO 30
<211> LENGTH: 808
<212> TYPE: DNA
<213> ORGANISM: Artificial sequence
<220> FEATURE:
<223> OTHER INFORMATION: First humanized 9012.2 scFv fragment VL
      nucleotide sequence

<400> SEQUENCE: 30
caggtgcagc tgcaggagag cggcgcggaa gtgaaaaaac cgggcgcgag cgtgaaagtg      60
agctgtaaag cgagcggcta tagctttacc agctataata tgcattgggt gcgtcaggcg    120
ccgggccagc gtctagaatg gatgggcggc atttatccgg caatggcga taccagcttt      180 aatcagaaat ttaaaggcaa agcgaccctg accgccgata aaagcagccg taccgcgtat     240
atgggcctga gcagcctgcg cccggaagac accgccgtgt attattgtgc cgtggcacc     300 gtggtgggcg attggtattt tgatgtgtgg ggccagggca cctggtgac cgtgagcagc      360 ggcgaggcg gatccggtgg tggcggatct ggaggtggcg aagcgatgt gctgatgacc       420 cagagcccga gcagcctgag cgccagcgtg ggcgatcgtg tgaacattgc ctgccgtagc     480
agccagagcc tggaaatgag caacggcaac acctatctga actggtatct ccagaaaccg     540
```
ggcaaagcgc cgcggctgct gatttatcgt gtgagcaacc gttttagcgg cgtgccgagc    600
cgctttagcg gctccggaag cggcaccgat tttaccctga ccattagcag cctccagccg    660
gaagattttg ccatctatta ttgcctccag ctgacccatg tgccgtggac ctttggtggc    720
ggcaccaaag tggaaatcaa acgctcgaga gttaccgtta gcagcgaaca gaaactgatt    780
agcgaagaag atctgaatta ataataag                                       808

<210> SEQ ID NO 31
<211> LENGTH: 360
<212> TYPE: DNA
<213> ORGANISM: Artificial sequence
<220> FEATURE:
<223> OTHER INFORMATION: First humanized 9012.2 scFv fragment complete
      nucleotide sequence

<400> SEQUENCE: 31
caggtgcagc tgcaggagag cggcgcggaa gtgaaaaaac cgggcgcgag cgtgaaagtg     60
agctgtaaag cgagcggcta tagctttacc agctataata tgcattgggt gcgtcaggcg    120
ccgggccagc gtctagaatg gatgggcggc atttatccgg gcaatggcga taccagcttt    180
aatcagaaat ttaaaggcaa agcgaccctg accgccgata aaagcagccg taccgcgtat    240
atgggcctga gcagcctgcg cccggaagac accgccgtgt attattgtgc gcgtggcacc    300
gtggtgggcg attggtattt tgatgtgtgg ggccagggca ccctggtgac cgtgagcagc    360

<210> SEQ ID NO 32
<211> LENGTH: 403
<212> TYPE: DNA
<213> ORGANISM: Artificial sequence
<220> FEATURE:
<223> OTHER INFORMATION: Humanized 9012.2 scFv fragment VL domain

<400> SEQUENCE: 32
gatgtgctga tgacccagag cccgagcagc ctgagcgcca gcgtgggcga tcgtgtgaac     60
attgcctgcc gtagcagcca gagcctggaa atgagcaacg gcaacaccta tctgaactgg    120
tatctccaga aaccgggcaa agcgccgcgg ctgctgattt atcgtgtgag caaccgtttt    180
agcggcgtgc cgagccgctt tagcggctcc ggaagcggca ccgatttttac cctgaccatt    240 agcagcctcc agccggaaga ttttgccatc tattattgcc tccagctgac ccatgtgccg    300
tggacctttg gtggcggcac caaagtggaa atcaaacgct cgagagttac cgttagcagc    360
gaacagaaac tgattagcga agaagatctg aattaataat aag                      403

<210> SEQ ID NO 33
<211> LENGTH: 23
<212> TYPE: DNA
<213> ORGANISM: Artificial sequence
<220> FEATURE:
<223> OTHER INFORMATION: Oligodesoxyribonucleotide

<400> SEQUENCE: 33
taatacgact cactagggcg aat                                             23

<210> SEQ ID NO 34
<211> LENGTH: 20
<212> TYPE: DNA
<213> ORGANISM: Artificial sequence
<220> FEATURE:
<223> OTHER INFORMATION: Oligodesoxyribonucleotide

<400> SEQUENCE: 34

-continued cggcagccgc tggattgtta                                              20

<210> SEQ ID NO 35
<211> LENGTH: 29
<212> TYPE: DNA
<213> ORGANISM: Artificial sequence
<220> FEATURE:
<223> OTHER INFORMATION: Oligodesoxyribonucleotide

<400> SEQUENCE: 35
cgagcttagc ccttataatt cagatcctc                                    29

<210> SEQ ID NO 36
<211> LENGTH: 68
<212> TYPE: DNA
<213> ORGANISM: Artificial sequence
<220> FEATURE:
<223> OTHER INFORMATION: Oligodesoxyribonucleotide

<400> SEQUENCE: 36
ggaggcggat ccggtggtgg cggatctgga ggtggcggaa gcgatgtttt gatgacccaa    60
actccact                                                           68

<210> SEQ ID NO 37
<211> LENGTH: 39
<212> TYPE: DNA
<213> ORGANISM: Artificial sequence
<220> FEATURE:
<223> OTHER INFORMATION: Oligodesoxyribonucleotide

<400> SEQUENCE: 37
accaccggat ccgcctccgc ctgaggagac ggtgaccgt                          39

<210> SEQ ID NO 38
<211> LENGTH: 30
<212> TYPE: DNA
<213> ORGANISM: Artificial sequence
<220> FEATURE:
<223> OTHER INFORMATION: Oligodesoxyribonucleotide

<400> SEQUENCE: 38
gaccctcgag cgtttgatct ccagcttggt                                   30

<210> SEQ ID NO 39
<211> LENGTH: 21
<212> TYPE: DNA
<213> ORGANISM: Artificial sequence
<220> FEATURE:
<223> OTHER INFORMATION: Oligodesoxyribonucleotide

<400> SEQUENCE: 39
ggcgactggt acttcgatgt c                                            21

<210> SEQ ID NO 40
<211> LENGTH: 24
<212> TYPE: DNA
<213> ORGANISM: Artificial sequence
<220> FEATURE:
<223> OTHER INFORMATION: Oligodesoxyribonucleotide

<400> SEQUENCE: 40
aaatggtgac acttccttca atca                                         24

<210> SEQ ID NO 41

```
<211> LENGTH: 24
<212> TYPE: DNA
<213> ORGANISM: Artificial sequence
<220> FEATURE:
<223> OTHER INFORMATION: Oligodesoxyribonucleotide

<400> SEQUENCE: 41
gttttcaagg ctctgactag acct                                              24

<210> SEQ ID NO 42
<211> LENGTH: 22
<212> TYPE: DNA
<213> ORGANISM: Artificial sequence
<220> FEATURE:
<223> OTHER INFORMATION: Oligodesoxyribonucleotide

<400> SEQUENCE: 42
ggattacagt tggtgcagca tc                                                22

<210> SEQ ID NO 43
<211> LENGTH: 21
<212> TYPE: DNA
<213> ORGANISM: Artificial sequence
<220> FEATURE:
<223> OTHER INFORMATION: Oligodesoxyribonucleotide

<400> SEQUENCE: 43
gayattgtgm tsacmcarwc t                                                 21

<210> SEQ ID NO 44
<211> LENGTH: 32
<212> TYPE: DNA
<213> ORGANISM: Artificial sequence
<220> FEATURE:
<223> OTHER INFORMATION: Oligodesoxyribonucleotide

<400> SEQUENCE: 44
cgggatcctc tagacagtgg ataracmgat gg                                     32

<210> SEQ ID NO 45
<211> LENGTH: 35
<212> TYPE: DNA
<213> ORGANISM: Artificial sequence
<220> FEATURE:
<223> OTHER INFORMATION: Oligodesoxyribonucleotide

<400> SEQUENCE: 45
cgggatcctc tagaggtsma rctgcagsag tcwgg                                  35

<210> SEQ ID NO 46
<211> LENGTH: 131
<212> TYPE: PRT
<213> ORGANISM: Artificial sequence
<220> FEATURE:
<223> OTHER INFORMATION: Second humanized 9012.2 scFv fragment VL amino
      acid sequence

<400> SEQUENCE: 46

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
```

Asp Arg Phe Ser Gly Ser Gly Ser Gly Thr Asp Phe Thr Leu Thr Ile
65                  70                  75                  80

Ser Ser Leu Gln Pro Glu Asp Phe Ala Ile Tyr Tyr Cys Leu Gln Leu
                85                  90                  95

Thr His Val Pro Trp Thr Phe Gly Gly Gly Thr Lys Val Glu Ile Lys
            100                 105                 110

Arg Ser Arg Val Thr Val Ser Ser Asp Gln Lys Leu Ile Ser Glu Glu
        115                 120                 125

Asp Leu Asn
        130

<210> SEQ ID NO 47
<211> LENGTH: 266
<212> TYPE: PRT
<213> ORGANISM: Artificial sequence
<220> FEATURE:
<223> OTHER INFORMATION: Second humanized 9012.2 scFv fragment complete
      amino acid sequence

<400> SEQUENCE: 47

Gln Val Gln Leu Gln Glu Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Asn Met His Trp Val Arg Gln Ala Pro Gly Gln Arg Leu Glu Trp Met
        35                  40                  45

Gly Gly Ile Tyr Pro Gly Asn Gly Asp Thr Ser Phe Asn Gln Lys Phe
    50                  55                  60

Lys Gly Lys Ala Thr Leu Thr Ala Asp Lys Ser Ser Arg Thr Ala Tyr
65                  70                  75                  80

Met Gly Leu Ser Ser Leu Arg Pro Glu Asp Thr Ala Val Tyr Tyr Cys
                85                  90                  95

Ala Arg Gly Thr Val Val Gly Asp Trp Tyr Phe Asp Val Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Asp Val Leu Met Thr Gln Thr Pro Leu
    130                 135                 140

Ser Leu Pro Val Ser Leu Gly Asp Gln Ala Ser Ile Ser Cys Arg Ser
145                 150                 155                 160

Ser Gln Ser Leu Glu Asn Ser Asn Gly Asn Thr Tyr Leu Asn Trp Tyr
                165                 170                 175

Leu Gln Lys Pro Gly Gln Ser Pro Gln Leu Leu Ile Tyr Arg Val Ser
            180                 185                 190

Asn Arg Phe Ser Gly Val Leu Asp Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Ile Tyr Tyr Cys Leu Gln Leu Thr His Val Pro Trp Thr Phe Gly Gly
225                 230                 235                 240

Gly Thr Lys Val Glu Ile Lys Arg Ser Arg Val Thr Val Ser Ser Asp
                245                 250                 255

Gln Lys Leu Ile Ser Glu Glu Asp Leu Asn
            260                 265

<210> SEQ ID NO 48
<211> LENGTH: 360
<212> TYPE: DNA
<213> ORGANISM: Artificial sequence
<220> FEATURE:
<223> OTHER INFORMATION: Second humanized 9012.2 scFv fragment VH
      nucleotide sequence

<400> SEQUENCE: 48

| | | | | | |
|---|---|---|---|---|---|
| caggtgcagc | tgcaggaaag | cggcgccgaa | gttaaaaaac | cgggcgccag | cgtgaaagtg | 60 |
| agctgtaaag | cgagcggcta | tagctttacc | agctataaca | tgcattgggt | tcgtcaggcg | 120 |
| ccgggtcagc | gtctagaatg | gatgggcggc | atttatccgg | caacggcga | taccagcttt | 180 |
| aaccagaaat | tcaaaggcaa | agcgaccctg | accgccgata | aaagcagccg | taccgcctat | 240 |
| atgggcctga | gcagcctgcg | cccggaagac | accgccgttt | attattgcgc | gcgtggcacc | 300 |
| gtggtgggcg | attggtattt | tgatgtgtgg | ggccagggca | ccctggttac | cgtgagcagc | 360 |

<210> SEQ ID NO 49
<211> LENGTH: 399
<212> TYPE: DNA
<213> ORGANISM: Artificial sequence
<220> FEATURE:
<223> OTHER INFORMATION: Second humanized 9012.2 scFv fragment VL
      nucleotide sequence

<400> SEQUENCE: 49

| | | | | | |
|---|---|---|---|---|---|
| gatgttttga | tgacccaaac | tccactctcc | ctgcctgtca | gtcttggaga | tcaagcctcc | 60 |
| atctcttgca | ggtctagtca | gagccttgaa | aacagtaatg | gaaacaccta | tttgaactgg | 120 |
| tacctccaga | aaccaggcca | gtctccacag | ctcctgatct | acagggtttc | caaccgattt | 180 |
| tctggggtcc | tagacaggtt | tagcggctcc | ggaagcggca | ccgatttcac | gctgaccatt | 240 |
| agcagcctgc | aaccggaaga | ttttgcgatt | tattattgtc | tgcaactgac | ccatgtgccg | 300 |
| tggaccttg | gcggcggcac | caaagtggaa | attaaacgct | cgagggtcac | cgtctcctca | 360 |
| gatcaaaaac | tcatctcaga | agaggatctg | aattaataa | | | 399 |

<210> SEQ ID NO 50
<211> LENGTH: 804
<212> TYPE: DNA
<213> ORGANISM: Artificial sequence
<220> FEATURE:
<223> OTHER INFORMATION: Second humanized 9012.2 scFv fragment complete
      nucleotide sequence

<400> SEQUENCE: 50

| | | | | | |
|---|---|---|---|---|---|
| caggtgcagc | tgcaggaaag | cggcgccgaa | gttaaaaaac | cgggcgccag | cgtgaaagtg | 60 |
| agctgtaaag | cgagcggcta | tagctttacc | agctataaca | tgcattgggt | tcgtcaggcg | 120 |
| ccgggtcagc | gtctagaatg | gatgggcggc | atttatccgg | caacggcga | taccagcttt | 180 |
| aaccagaaat | tcaaaggcaa | agcgaccctg | accgccgata | aaagcagccg | taccgcctat | 240 |
| atgggcctga | gcagcctgcg | cccggaagac | accgccgttt | attattgcgc | gcgtggcacc | 300 |
| gtggtgggcg | attggtattt | tgatgtgtgg | ggccagggca | ccctggttac | cgtgagcagc | 360 |
| ggcggtggtg | gatccggtgg | tggcggatct | ggaggtggcg | gaagcgatgt | tttgatgacc | 420 |
| caaactccac | tctccctgcc | tgtcagtctt | ggagatcaag | cctccatctc | ttgcaggtct | 480 |
| agtcagagcc | ttgaaaacag | taatggaaac | acctatttga | actggtacct | ccagaaacca | 540 |
| ggccagtctc | cacagctcct | gatctacagg | gtttccaacc | gattttctgg | ggtcctagac | 600 |

```
aggtttagcg gctccggaag cggcaccgat tcacgctga ccattagcag cctgcaaccg    660
gaagattttg cgatttatta ttgtctgcaa ctgacccatg tgccgtggac ctttggcggc    720
ggcaccaaag tggaaattaa acgctcgagg gtcaccgtct cctcagatca aaaactcatc    780
tcagaagagg atctgaatta ataa                                            804
```

```
<210> SEQ ID NO 51
<211> LENGTH: 53
<212> TYPE: PRT
<213> ORGANISM: Artificial sequence
<220> FEATURE:
<223> OTHER INFORMATION: 1x9Q VL Sequence

<400> SEQUENCE: 51

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Val His Asn Ser
            20                  25                  30

Asn Gly Asn Thr Tyr Arg Asn Trp Tyr Leu Gln Lys Pro Gly Gln Ser
        35                  40                  45

Lys Val Leu Leu Ile
    50

<210> SEQ ID NO 52
<211> LENGTH: 122
<212> TYPE: PRT
<213> ORGANISM: Artificial sequence
<220> FEATURE:
<223> OTHER INFORMATION: VH 1VGE Sequence

<400> SEQUENCE: 52

Gln Val Lys Leu Leu Glu Gln Ser Gly Ala Glu Val Lys Lys Pro Gly
1               5                   10                  15

Ala Ser Val Lys Val Ser Cys Lys Ala Ser Gly Tyr Ser Phe Thr Ser
            20                  25                  30

Tyr Gly Leu His Trp Val Arg Gln Ala Pro Gly Gln Arg Leu Glu Trp
        35                  40                  45

Met Gly Trp Ile Ser Ala Gly Thr Gly Asn Thr Lys Tyr Ser Gln Lys
    50                  55                  60

Phe Arg Gly Arg Val Thr Phe Thr Arg Asp Thr Ser Ala Thr Thr Ala
65                  70                  75                  80

Tyr Met Gly Leu Ser Ser Leu Arg Pro Glu Asp Thr Ala Val Tyr Tyr
                85                  90                  95

Cys Ala Arg Asp Pro Tyr Gly Gly Gly Lys Ser Glu Phe Asp Tyr Trp
            100                 105                 110

Gly Gln Gly Thr Leu Val Thr Val Ser Ser
        115                 120

<210> SEQ ID NO 53
<211> LENGTH: 108
<212> TYPE: PRT
<213> ORGANISM: Artificial sequence
<220> FEATURE:
<223> OTHER INFORMATION: VL 1VGE Sequence

<400> SEQUENCE: 53

Glu Leu Val Leu Met Thr Ser Thr Ser Leu Ser Ser Ala Val Val Leu
1               5                   10                  15

Gly Arg Val Asn Ser Ala Ser Cys Arg Ser Ser Gly Ile Ser Ser Ala
            20                  25                  30
```

-continued

```
Leu Ala Trp Tyr Gln Gln Lys Pro Gly Lys Ala Pro Arg Leu Leu Ile
        35                  40                  45

Tyr Asp Ala Ser Asn Leu Asp Ser Gly Val Pro Ser Asp Arg Phe Ser
        50                  55                  60

Gly Ser Gly Ser Gly Thr Asp Phe Thr Thr Lys Ile Ser Leu Gln Pro
65                  70                  75                  80

Ala Glu Phe Ala Ile Val Tyr Tyr Cys Gln Gln Phe Asn Ser Val Pro
                85                  90                  95

Leu Thr Phe Gly Gly Gly Thr Val Leu Glu Ile Lys
                100             105
```

US 9,045,538 B2

ANTI-GLYCOPROTEIN VI SCFV FRAGMENT FOR TREATMENT OF THROMBOSIS

TECHNICAL FIELD

The present invention relates to a single chain variable fragment (scFv 9O12.2) directed against human glycoprotein VI, constituted of the VH and VL domains of 9O12.2 monoclonal antibody linked via a $(Gly_4Ser)_3$ peptide and followed by a "c-myc" flag, represented by SEQ ID NO:1. The invention also concerns functional variants of said scFv 9O12.2 fragment with identical heavy and light chains complementary determining regions 1, 2 and 3, and preferably humanized functional variants such as the humanized scFv fragments represented by SEQ ID NO:28 or SEQ ID NO:47. The invention also relates to nucleic acids encoding such a scFv fragment, expression vectors and host cells to produce such a scFv fragment, as well as therapeutic uses of such a scFv fragment.

BACKGROUND ART

Acute coronary and cerebrovascular accidents are currently the first death cause in the world. In addition, the global incidence of recurrence and death in the 6 month post-treatment period after an acute coronary syndrome is still 8-15%. In the case of acute coronary syndrome with ST segment elevation, mechanical treatment with coronary angioplasty and introduction of a stent is highly efficient to urgently restore coronary artery flow, but does not prevent morbidity/mortality for about 15% of patients in the next 6 months.

Thrombolytic treatments, which are based on long term fibrinolytic, anticoagulant and anti-aggregating drugs associations, give even less encouraging results. Indeed, despite improvements in medical treatment of thrombosis, morbidity/mortality at 6 months is similar to that observed for acute coronary syndrome without segment ST elevation.

Concerning cerebrovascular ischemic accidents, treatments are still very limited due to the generally late caring of most patients and to the hemorrhagic risk of currently available anti-thrombotic treatments.

There is thus a real pressing clinical need for improving treatments for cardiovascular diseases, and especially for new molecules with improved features compared to available molecules, in particular for molecules with a reduced hemorrhagic effect.

Platelets-collagen interactions are critical in the appearance of acute arterial thrombosis and post-thrombotic vascular remodeling. Glycoprotein VI (GPVI), the main receptor for platelets activation by collagen, has been demonstrated in animals to play a role in experimental thrombosis, vascular remodeling, atherothrombosis and acute myocardial ischemia.

Contrary to αIIbβ3 integrin antagonists, which are currently used in thrombosis treatment and inhibit platelets final activation phase, GPVI is implicated into platelets initial activation phase, and GPVI antagonists should thus prevent not only platelet aggregation, but also secondary agonists liberation as well a growth factors and cytokines secretion resulting into vascular lesions development. In addition, GPVI deficit is not associated with a high hemorrhagic risk, which is a crucial feature for patient's safety. Finally, GPVI expression is limited to platelets, and thus represents a perfectly specific target for anti-thrombosis treatment.

GPVI antagonists should thus be efficient for specifically and efficiently preventing primary or secondary thrombosis, while involving only a low hemorrhagic risk.

Various kinds of potential GPVI antagonists have been generated. In one approach, a soluble GPVI recombinant protein has been generated, which is a fusion protein between GPVI extracellular domain and human Ig Fc domain (see for instance WO 01/00810 (1) and WO 03/008454 (2)). Thus soluble recombinant GPVI protein competes with platelet GPVI for binding collagen. Encouraging results were first obtained with this soluble GPVI protein in a thrombosis murine model (3), but these results were not confirmed (4). In addition, this approach involves structural, functional and pharmacological disadvantages. First, this compound is a high molecular weight protein (~160 kDa) the half life of which is expected to be short. Since GPVI contains at least one cleavage site for proteases, the hydrolysis of the soluble recombinant GPVI-Fc protein has to be envisaged. When bound to collagen, the protein will expose its Fc domain to the blood stream. Human platelets (but not mice platelets) and leucocytes express the low affinity Fc receptor (FcγRIIA) at their surface. Cross-linking of the platelet FcγRIIA by immobilized GPVI-Fc is susceptible to activate platelets and thus to have an opposite effect to the one expected. The timing and the dose to which the protein should be administrated also cause problem. Once bound to collagen platelets are rapidly and irreversibly activated. Thus, to be effective GPVI-Fc should be administrated before platelet activation that is before the thrombotic event, a situation rare in current medicine. Furthermore, the amount of protein that should be administrated will vary as a function of the size and the nature of the vascular lesion, a parameter impossible to predict.

Many others have tried to develop neutralizing monoclonal antibodies directed against human GPVI. For instance, EP 1224942 (5) and EP 1228768 (6) disclose a monoclonal anti-GPVI antibody JAQ1, which specifically binds to mouse GPVI, for the treatment of thrombotic disease. JAQ1 antibody induces irreversible internalization of the GPVI receptor on mouse platelets.

EP1538165 (7) describes another monoclonal anti-GPVI antibody hGP 5C4, which Fab fragment was found to have marked inhibitory effects on the main physiological functions of platelets induced by collagen stimulation: stimulation of collagen-mediated physiological activation parameters PAC-1 and CD 62P-Selectin was completely prevented by hGP 5C4 Fab, and hGP 5C4 Fab potently inhibited human platelet aggregation ex viva without any intrinsic activity.

WO 2005/111083 (8) describes 4 monoclonal anti-GPVI antibodies OM1, OM2, OM3 and OM4, that were found to inhibit GPVI binding to collagen, collagen-induced secretion and thromboxane A2 (TXA2) formation in vitro, as well as ex vivo collagen-induced platelet aggregation after intravenous injection to Cynomolgus monkeys. OM4 also appears to inhibit thrombus formation in a rat thrombosis model.

WO 01/00810 (1) also describes various monoclonal anti-GPVI antibodies named 7I20.2, 8M14.3, 3F8.1, 9E18.3, 3J24.2, 6E12.3, IP10.2, 4L7.3, 7H4.6, 9O12.2, 7H14.1, and 9E18.2, as well as several scFv fragments named A9, A10, C9, A4, C10, B4, C3 and D11. Some of these antibodies and scFv fragments were found to inhibit GPVI binding to collagen, including antibodies 8M14.3, 3F8.1, 9E18.3, 3J24.2, 6E12.3, IP10.2, 4L7.3, 7H4.6, and 9O12.2, and scFv fragments A10, A4, C10, B4, C3 and D11.

In addition, 9O12.2 Fab fragments were found to completely block collagen-induced platelet aggregation and secretion, to inhibit the procoagulant activity of collagen-stimulated platelets and platelet adhesion to collagen in static conditions, to impair platelet adhesion, and to prevent thrombi formation under arterial flow conditions (9).

However, none of the currently known anti-GPVI antibodies have proven really efficient in vivo for preventing and/or treating cardiovascular diseases implicating platelet aggregation such as arterial and venous thrombosis, restenosis, acute coronary syndrome, and cerebrovascular accidents due to atheroscleroris. Until recently the different anti-GPVI antibodies that have been reported appeared not fitted for the development of an antithrombotic for medical use in human. Only few antibodies have been reported to have inhibitory properties. This is the case of JAQ1 that is directed to mouse GPVI and does not cross react with human GPVI (10). Human scFvs directed to human GPVI have also been reported to be inhibitory (11,12) but their affinity appears to be low. Very recently, new inhibitory antibodies with a good affinity for human GPVI have been characterised (13) and proposed to be developed as therapeutic tools.

However, cross-linking of GPVI at the platelet surface by a divalent or multivalent ligand results in platelet activation. This is the case of the 9O12.2 IgGs that activate platelets via GPVI dimerisation and via cross-linking of GPVI to the low affinity Fc receptor (FcγRIIA) (9). Fab'$_2$ also activate platelets via GPVI dimerisation (9). In contrast, monovalent 9O12.2 Fab fragments are inhibitory. However these fragments could not be used in therapeutic due to their size and their animal origin which makes them immunogenic in human patients.

There is thus still a need for an efficient neutralizing GPVI antagonist, which would inhibit with high efficiency the initial phase of platelets aggregation, with a low hemorrhagic risk, as well as a low immunogenic effect.

DISCLOSURE OF THE INVENTION

From the 9O12.2 monoclonal anti-GPVI antibody hybridoma, the inventors have generated a single chain variable fragment (scFv) 9O12.2 which has the advantage to contain the functional inhibitory motif in a fragment of reduced size without any immunogenic constant domains (CH$_1$ and CL). The scFv is the starting material to produce fragments with an improved immune tolerance and stability in order to obtain a format adapted to a therapeutic use.

Technologic approaches to design such fragments have previously been reported in details, however there are many difficulties to overpass making each scFv construct a specific case. These difficulties include the cloning of antibody V-genes by bypassing aberrant transcripts (14), identification of a linker well-suited for correct folding, association of V-domains into a monomeric scFv and finally the selection of a procaryotic expression system that enable expression of the scFv in a functional soluble form.

The invention thus concerns a single chain variable fragment directed against human glycoprotein VI, comprising:

a VH domain comprising CDR1, CDR2 and CDR3 regions constituted of SEQ ID NO: 2, SEQ ID NO: 3, and SEQ ID NO: 4, a peptide linker, and a VL domain comprising CDR1, CDR2 and CDR3 regions constituted of SEQ ID NO: 5, SEQ ID NO: 6, and SEQ ID NO: 7.

In a preferred embodiment, said scFv fragment according to the invention further comprises a peptide tag, useful for purification, and optionally a short peptide spacer between the core scFv fragment (comprising the VH and VL domains and the peptide linker) and the peptide tag.

An antibody is a roughly Y-shaped molecule composed of two different polypeptide chains named "heavy" and "light" chains, an antibody being constituted of two heavy and two light chains linked by disulfide bonds. Each heavy chain is composed of a variable domain ("VH domain") and 3 constant domains ("CH1", "CH2" and "CH3" domains), while each light chain is composed of a variable domain ("VL domain") and a constant domain ("CL domain").

A "single chain variable fragment" or "scFv fragment" refers to a single folded polypeptide comprising the $V_H$ and $V_L$ domains of an antibody linked through a linker molecule. In such a scFv fragment, the $V_H$ and $V_L$ domains can be either in the $V_H$-linker-$V_L$ or $V_L$-linker-$V_H$ order. In addition to facilitate its production, a scFv fragment may contain a tag molecule linked to the scFv via a spacer. A scFv fragment thus comprises the $V_H$ and $V_L$ domains implicated into antigen recognizing but not the immunogenic constant domains of corresponding antibody.

In addition, each variable domain (VH or VL domain) is composed of 4 "framework regions" (FR1, FR2, FR3 and FR4), which display less variability among antibodies and are involved in the formation of β sheets forming the structural framework of the variable domain, and of 3 hypervariable regions commonly named "complementary determining regions" 1, 2 and 3 (CDR1, CDR2, CDR3), which correspond to 3 loops juxtaposed in the folded variable domain at the edge of each β sheet. The 3 CDR regions are crucial for determining an antibody or antibody fragment specificity since they are the part of the variable domain mainly in contact with the antigen, especially the CDR3 region of each chain, which corresponds to the rearranged region of the heavy and light chains and is even more variable and more directly in contact with the specific antigen.

Thus, the invention encompasses all functional variants of scFv 9O12.2 which keep identical CDR regions. The scFv fragment 9O12.2 CDR regions data are presented in following Table 1:

TABLE 1 scFv 9O12.2 CDR regions. CDR regions were identified using Kabat and Chotia nomenclature (15, 16)

| CDR | Position in scFv 9O12.2 (aa) | Sequence |
| --- | --- | --- |
| VH CDR1 | 26-35 | GYTFTSYNMH (SEQ ID NO: 2) |
| VH CDR2 | 50-66 | GIYPGNGDTSFNQKFKG (SEQ ID NO: 3) |
| VH CDR3 | 99-109 | GTVVGDWYFDV (SEQ ID NO: 4) |
| VL CDR1 | 159-174 | RSSQSLENSNGNTYLN (SEQ ID NO: 5) |

TABLE 1-continued scFv 9012.2 CDR regions. CDR regions were identified using Kabat and Chotia nomenclature (15, 16)

| CDR | Position in scFv 9012.2 (aa) | Sequence |
| --- | --- | --- |
| VL CDR2 | 190-196 | RVSNRFS (SEQ ID NO: 6) |
| VL CDR3 | 229-237 | LQLTHVPWT (SEQ ID NO: 7) |

By a "peptide linker" is meant a flexible peptide that permits an appropriate folding of the scFv fragment, ie an appropriate folding of the VH and VL domains and their capacity to be brought together. In addition, such a peptide linker should permit folding into a monomeric functional unit. When the scFv is assembled in the VH to VL orientation ($V_H$-linker-$V_L$), an scFv with a linker of 3 to 12 residues cannot fold into a functional Fv domain and instead associates with a second molecule to form a bivalent dimer. Reducing below 3 residues leads to trimers. In this case, a suitable linker should thus have at least 12 and preferably less than 25 aminoacids, preferably between 14-18, 14-16, or 15 amino acids, and should preferably comprise a high percentage of glycine residues, preferably at least 50%. Examples of suitable peptide linkers include peptides $(G_4S)_3$ (SEQ ID NO:8), $G_4IAPSMVG_4S$ (SEQ ID NO:9), $G_4KVEGAG_5S$ (SEQ ID NO:10), $G_4SMKSHDG_4S$ (SEQ ID NO:11), $G_4NLITIVG_4S$ (SEQ ID NO:12), $G_4VVPSLG_4S$ (SEQ ID NO:13) and $G_2EKSIPG_4S$ (SEQ ID NO:14). When the scFv is produced in the VL to VH orientation ($V_L$-linker-$V_H$), the distance between the C-terminus of VL and N-terminus of VH is slightly greater than between the C-terminus of VH and N-terminus of VL (39-43 Å versus 30-34 Å). Therefore, a 18 amino acid residues linker is the minimal sequence size that can be used. A suitable peptide linker should then have between 18-25 aa, preferably between 18-21 aa. An example of a suitable linker is linker of sequence GSTSGSGKSSEGSGSTKG (SEQ ID NO: 15).

By a "peptide tag" is meant a peptide of 5-15 amino acids for which specific antibodies are available. Although optional in a scFv fragment according to the invention, such a peptide tag inserted at the C-terminal end of the scFv fragment permits to facilitate purification of the scFv fragment after recombinant production. Indeed, the peptide tag gives the protein a specific binding affinity it would not otherwise, which permits an easier purification using chromatography. Examples of suitable peptide tags include a His6 tag (HHHHHH, SEQ ID NO:16), which has affinity towards nickel ions and can thus be purified using a nickel ions containing chromatography column, or epitopes peptides with high affinity for their specific antibody and can thus be purified using a column containing immobilized antibody directed against peptide, such as a c-myc tag (EQKLISEEDLN, SEQ ID NO:17), a HA tag (YPYDVPDYA, SEQ ID NO:18), a Flag tag (DYKDDDDK, SEQ ID NO:19) a protein C tag (EDQVDPRLIDGK, SEQ ID NO:20), a Tag-100 tag (EETARFQPGYRS, SEQ ID NO:21), a V5 epitope tag (GKPIPNPLLGLDST, SEQ ID NO:22), a VSV-G tag (YTDIEMNRLGK, SEQ ID NO:23) or a Xpress tag (DLYDDDDK, SEQ ID NO:24).

By a "short peptide spacer" is meant a peptide of 1-15 amino acids, preferably 1-12 or 1-10 amino acids, for instance 8 amino acids. Such a peptide spacer is intended to separate the true scFv part (VH and VL domains separated by a peptide linker) of the optional peptide tag. It is not necessary in a scFv fragment according to the invention, in particular when there is no peptide tag, but also when a peptide tag is included. Indeed a peptide tag may be directly fused to the VH or VL domain. However, a short peptide spacer of 1-12 amino acids may be useful. For instance, in the 9O12.2 scFv fragment, a 8 amino acids peptide spacer of sequence RSRVTVSS (SEG ID NO: 25) has been used.

In a preferred embodiment, the invention concerns a single chain variable fragment (scFv) directed against human glycoprotein VI, comprising or consisting of an amino acid sequence having at least 95%, at least 96%, at least 97%, at least 98%, at least 98.5%, at least 99%, at least 99.5%, at least 99.6%, at least 99.7%, at least 99.8%, identity with SEQ ID NO:1, in which amino acids 26 to 35, 50 to 66, 99 to 109, 159 to 174, 190 to 196, and 229 to 237 of said 266 amino acids sequence are constituted of SEQ ID NO: 2, SEQ ID NO:3, SEQ ID NO:4, SEQ ID NO:5, SEQ ID NO:6, and SEQ ID NO:7 respectively. Such functional variants of scFv 9O12.2 not only keep identical CDR regions but also have a high identity percentage with the amino acid sequence of scFv 9O12.2. In a particular embodiment, the invention concerns a single chain variable fragment comprising or consisting of SEQ ID NO:1.

However, framework regions may be mutated to generate a chimeric, in particular humanized, scFv fragment directed against human glycoprotein VI. With regards to a reference antibody or antibody fragment of a given species, a corresponding "chimeric" antibody or antibody fragment in which framework regions have been replaced by corresponding framework regions of another species. More particularly, a "humanized" antibody or antibody fragment is an antibody or antibody fragment with identical CDR regions in which framework regions have been replaced by human framework regions.

The scFv 9O12.2 fragment has been derived by the inventors from murine monoclonal antibody 9O12.2, and thus has mouse framework regions. However, to reduce immunogenic effect of injection of this fragment in human patients, a humanized scFv fragment may be desirable, in which murine framework regions have been replaced by human framework regions.

Several possible methods of humanizing antibody V-domains have been suggested. They include CDR-grafting, resurfacing V-domains or predictive computational analysis that explores a diversity of substitutions in a given V chain sequence with the aim of reducing immunogenicity whilst maintaining the antigen-specificity and affinity of the original molecule (17-19). None of these methods is simple, and all often result in impaired specificity and/or affinity (20-23).

Despite these difficulties, the inventors have generated a first humanized scFv fragment in which the $V_H$ and $V_L$ domains of murine 9O12.2 scFv fragment, corresponding to amino acids number 1-120 and 136-266 of SEQ ID NO:1, have been respectively replaced by humanized $V_H$ and $V_L$ domains SEQ ID NO:26 and SEQ ID NO:27, resulting in a humanized scFv fragment of amino acid sequence SEQ ID NO:28 (hscFv 9O12.2 (1), see FIG. 14).

In a first preferred embodiment, the invention thus concerns a single chain variable fragment according to any of claims 1-3, in which framework regions of the $V_H$ and $V_L$ domains have been replaced by $V_H$ and $V_L$ domains having framework regions of a human antibody. In particular, said VH and VL domains may have been replaced respectively by SEQ ID NO:26 and SEQ ID NO:27. More precisely, when an scFv fragment comprising or consisting of SEQ ID NO:1 is humanized, it may result in a first humanized scFv fragment comprising or consisting of SEQ ID NO:28 (hscFv 9O12.2 (1), see FIG. 14).

To generate such a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322 (24); WO 87/02671 (25); U.S. Pat. No. 5,859,205 (26); U.S. Pat. No. 5,585,089 (27); U.S. Pat. No. 4,816,567 (28); EP0173494 (29); and references 20-21 and 30-31) or performing database searches to identify potential candidates. In a typical method aided by computer modeling and comparison to human germline sequences, the antigen binding loops of the monoclonal antibody to be humanized are superimposed onto the best fitting frameworks. The approach to humanize the scFv 9O12.2 has been adapted from CDR grafting technology (32). The CDRs of murine 9O12.2 antibody have been grafted on a human variable-chain framework. The choice of the human antibody has been done using the following criteria: the crystallographic structure has been elucidated (1VGE in pdb library); the variable domains of the human antibody 1VGE present a high degree of sequence homology with the variable domains of 9O12.2 (VH 60,6%; VL 55,4%); Structure comparison of the crystallographic data of the candidate human antibody 1VGE and the model of the variable domains of 9O12.2 was done and allowed us to validate the choice of the human acceptor scaffold 1 VGE. This strategy minimizes the risk of lowering the stability of the interaction between VH and VL domains while preserving the scaffold required for correct folding of the CDR, preserving a high affinity for the antigen. The human antibody 1VGE selected based on these analysis allowed to construct the humanized 9O12.2 scFv. For structural raisons, 10 residues after CDR H2 were not mutated. The nucleotide sequence encoding the humanized scFv 9O12.2 was optimized. First, restriction sites between CDR regions were introduced to make possible adjustments for optimal binding characteristics. Optimization was then performed using the bacterial codon usage in order to express the humanized scFv in the procaryotic expression system *E. coli*. Said method resulted in a humanized 9O12.2 scFv fragment in which $V_H$ and $V_L$ domains of the murine 9O12.2 scFv fragment, corresponding to amino acids number 1-120 and 136-266 of SEQ ID NO:1 respectively, have been replaced by SEQ ID NO:26 and SEQ ID NO:27 respectively, i.e. a humanized 9O12.2 scFv fragment consisting of SEQ ID NO: 28. In a preferred embodiment of a humanized scFv fragment according to the invention, said scFv fragment thus comprises or consists of SEQ ID NO:28.

Despite promising results obtained with this first humanized scFv fragment, this fragment was not optimal for production in bacteria, and a further optimized second humanized scFv fragment (hscFv 9O12.2(2)) was derived from hscFv 9O12.1(1). Briefly, for VL FR1 and FR2 regions, the identity with 1VGE frameworks 1 and 2 were low and the original 9O12 VL FR1 and FR2 were thus preserved in the second humanized scFv construction. Other refinements were carried out on the basis of close inspection of the model (see Example 2 for more details).

Thus, in a second preferred embodiment, the invention thus concerns a single chain variable fragment according to any of claims 1-3, in which framework regions of the $V_H$ and $V_L$ domains have been replaced by $V_H$ and $V_L$ domains having framework regions of a human antibody. In particular, said VH and VL domains may have been replaced respectively by SEQ ID NO: 26 and SEQ ID NO: 46. More precisely, when an scFv fragment comprising or consisting of SEQ ID NO: 1 is humanized, it may thus also preferably result in a second humanized scFv fragment comprising or consisting of SEQ ID NO: 47 (hscFv 9O12.2 (2), see FIG. 18).

The invention further concerns a nucleic acid sequence encoding a single chain variable fragment according to the invention as described before. In a particular embodiment, when said scFv fragment comprises or consists of SEQ ID NO: 1, said nucleic acid sequence may comprise or consist of SEQ ID NO:29, or any derived nucleic sequence encoding SEQ ID NO:1, for instance as a result of the degeneracy of the genetic code.

When said scFv fragment is humanized and $V_H$ and $V_L$ domains of the murine 9O12.2 scFv fragment, corresponding to amino acids number 1-120 and 136-266 of SEQ ID NO:1 respectively, have been replaced by SEQ ID NO:26 and SEQ ID NO:27 respectively, resulting in a first humanized 9O12.2 scFv fragment (hscFv 9O12.2(1)) comprising or consisting of SEQ ID NO:28, said nucleic acid may comprise or consist of SEQ ID NO:30, or any derived nucleic sequence encoding SEQ ID NO:28, for instance as a result of the degeneracy of the genetic code.

Alternatively, when said scFv fragment is humanized and $V_H$ and $V_L$ domains of the murine 9O12.2 scFv fragment, corresponding to amino acids number 1-120 and 136-266 47 respectively, resulting in a second humanized 9O12.2 scFv fragment (hscFv 9O12.2(2)) comprising or consisting of SEQ ID NO:47, said nucleic acid may comprise or consist of SEQ ID NO:50 (see FIG. 18C), or any derived nucleic sequence encoding SEQ ID NO:47, for instance as a result of the degeneracy of the genetic code.

The invention also concerns an expression vector comprising a nucleic acid sequence as described. Such an expression vector also comprises appropriate nucleic acid sequences necessary for the expression of the operably linked scFv coding sequence in a particular host cell. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals in a host cell.

Such an expression vector may also contain a leader sequence directing the expressed scFv to a particular cellular compartment, for instance a sequence directing a membrane expression or a secretion of the scFv fragment, or directing its expression in periplasm of bacteria. It may also contain under control of the same promoter a selection gene, the expression of which may be easily detected to select recombinant host cells transformed with the expression vector. Suitable selection genes include notably antibiotics resistance genes, fluorescent genes, or any other gene which expression may be easily monitored known by a person skilled in the art.

The invention further concerns a host cell comprising an expression vector as described above. Such a recombinant host cell may be obtained by transfecting or transforming a host cell with an expression vector according to the invention.

Such a host cell may be either prokaryotic or eukaryotic. Suitable prokaryotic host cells include gram-positive and gram-negative bacteria. Among gram-negative bacteria, a preferred host cell is represented by E. coli. For use in bacteria, the expression vector may preferably contain a leader sequence directing the expression of the scFv fragment into bacterial periplasm, corresponding to the space between the plasma membrane and the outer membrane of gram-negative bacteria or between the plasma membrane and the peptidoglycan layer (cell wall) of gram-positive bacteria. Suitable sequences directing the expression of a polypeptide to bacteria periplasm include ompA, ompF, ompT, LamB, β-lactamase, cp VIII from M13, pelB, malE or phoA signal peptides or leader sequences. In a particular embodiment, said leader sequence is pelB.

Alternatively, a eukaryotic cell may be used, in particular a mammalian cell. Indeed, this may permit to directly generate a glycosylated scFv fragment. Mammalian cell lines available as hosts for expression are known in the art and include many immortalized cell lines available notably from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines. As eukaryotic cells, yeast cells may also be used. To obtain a glycosylation pattern closest to a natural human glycosylation pattern, it may be resorted to human cell lines as host cells. Alternatively, Pichia pastoris yeast cells, a robust organism commonly used in fermentation processes which can be grown to high cell density in a chemically defined growth medium, have been modified by first eliminating endogenous yeast glycosylation pathways, while sequentially engineering into the organism a synthetic in vivo glycosylation pathway that enables the yeast to produce a complex human N-glycan, GlcNAc2Man3GlcNAc2, in vivo (see EP1297172 (33), EP1522590 (34), and references 35, 36). Such modified yeast cells with a humanized glycosylation pathway are able to secrete a human glycoprotein with uniform complex N-glycosylation.

The invention also concerns a method for preparing a single chain variable fragment according to the invention as described above, comprising:
a) culturing a host cell according to the invention as described above, and
b) purifying said single chain variable fragment.

Protocols and media for culturing host cells represent routine procedures and are readily available to any person skilled in the art. Concerning purification of the obtained scFv fragment, it may be performed using well-known technologies, including affinity chromatography (e.g., using protein L-Sepharose) or ion-exchange chromatography, hydroxylapatite chromatography, gel electrophoresis, dialysis, etc. More precisely, when the scFv fragment comprises a His6 tag or an epitope tag as described above, HPLC with nickel ion columns or with columns containing immobilized specific antibodies.

The invention further concerns a single chain variable fragment according to the invention as described above, as a medicament.

The invention also relates to a pharmaceutical composition, comprising a single chain variable fragment according to the invention as described above and a pharmaceutically acceptable carrier.

More precisely, the invention also concerns the use of a single chain variable fragment according to the invention as described above for preparing a medicament for treating and/or preventing a cardiovascular disease selected from arterial and venous thrombosis, restenosis, acute coronary syndrome, and cerebrovascular accidents due to atheroscleroris. In a preferred embodiment of such a use, said cardiovascular disease is thrombosis.

Having generally described this invention, a further understanding of characteristics and advantages of the invention can be obtained by reference to certain specific examples and figures which are provided herein for purposes of illustration only and are not intended to be limiting unless otherwise specified.

DESCRIPTION OF FIGURES

FIG. 2. Nucleotide SEQ ID NO:50 and deduced amino-acid (SEQ ID NO:1) sequences of scFv 9O12.2 cloned into plasmid pSWscFv9O12.2myc. Nucleotide and deduced amino-acid sequences of scFv 9O12.2 loned between the restriction sites Pst1 and Xho1 into the expression vector pSW1. The nucleotide sequences corresponding to the primers used for PCR amplification or encoding the linker peptide are shown in italics. The deduced amino-acid sequence of the complementary determining regions (CDRs) of VH and VL are underlined. The deduced amino-acid sequence of the c-myc flag is shown.

FIG. 5. Periplasmic production and affinity-chromatography purification of a recombinant protein from pSW1-scFv9O12.2myc cultures in E. coli Topp1. (A): SDS-PAGE stained with Coomassie Brillant Blue. (B): Western blot analysis with anti-c-myc IgG. Lane 1, Molecular mass standards; lane 2, periplasmic fraction of induced bacteria loaded onto a GPVI-sepharose column; lane 3, GPVI-sepharose column flow through fraction; lane 4 GPVI-sepharose column eluted fraction.

(B): scFv 9O12.2 (60 µg.mL$^{-1}$) binding in competition with increasing amounts of IgG 9O12.2.

Figure 8:
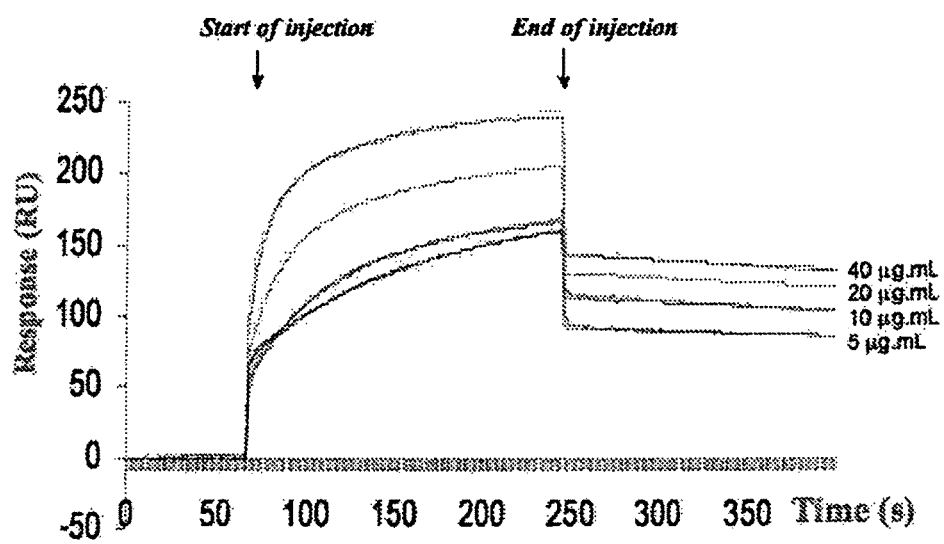

FIG. 8. Surface Plasmon Resonance analysis of scFv 9O12.2 binding to immobilized GPVI-Fc. scFv 9O12.2 affinity for GPVI-Fc is high with a $K_D$ in the order of $2.5 \times 10^{-9}$ M. $K_D$ of IgG and Fab 9O12.2.2 for GPVI-Fc are also in the nanomolar order ($6.5 \times 10^{-9}$ M and $4.5 \times 10^{-9}$ M respectively).

Figure 9:
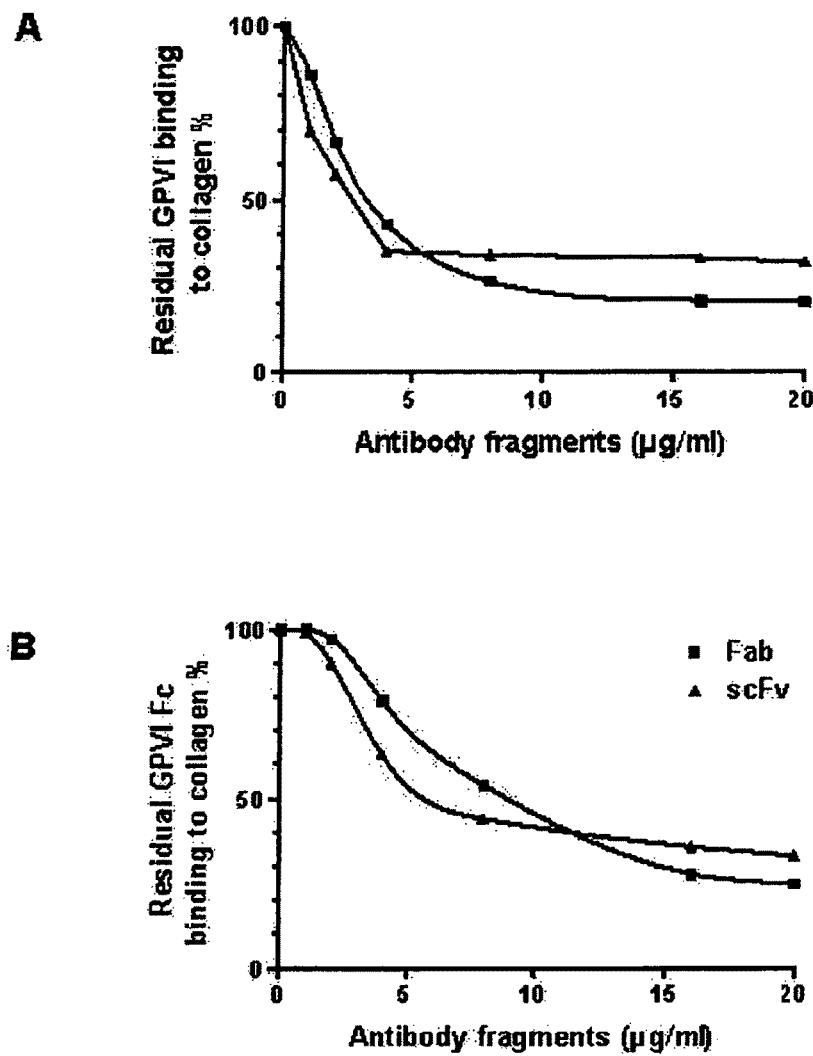

FIG. 9. Inhibition of GPVI binding to immobilized collagen. GPVI-Fc was incubated on immobilized collagen in the presence of increasing amounts of antibodies: scFv 9O12.2 (triangle), or pFab (square) (A): 2 µg of GP VI-Fc; (B): 4 µg of GPVI-Fc Bound GPVI-Fc was detected using an HRP coupled anti-Fc IgG.

Figure 10:
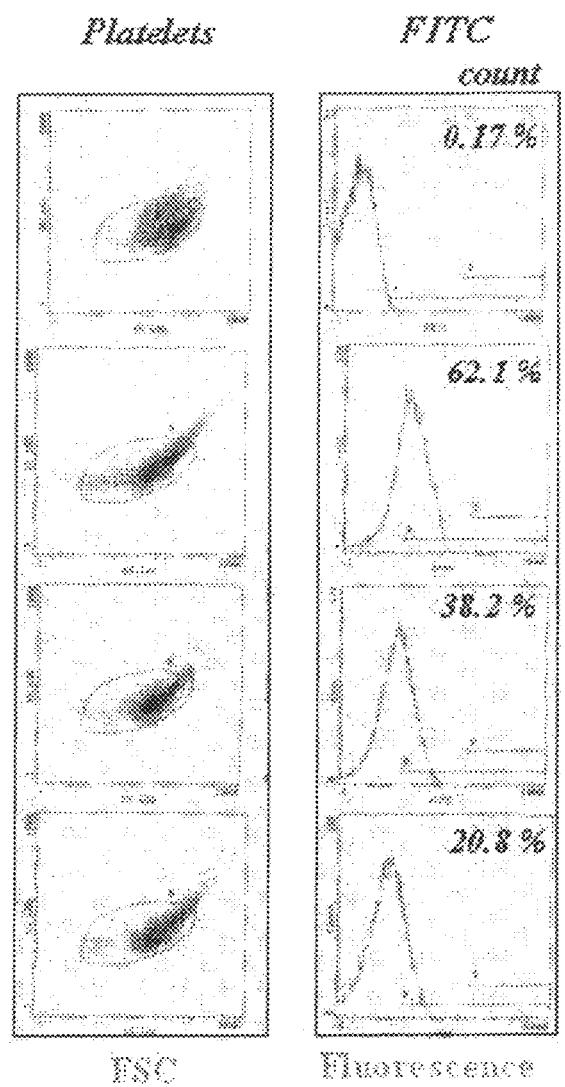

FIG. 10. Binding of purified scFv 9O12.2 to platelets: Flow cytometry analysis. Washed platelets were incubated with an irrelevant scFv (top) or decreasing amounts of scFv 9O12.2 (100, 50 and 25 mM). Binding of scFvs was analysed using an FITC-coupled anti-c-myc IgG.

Figure 11:
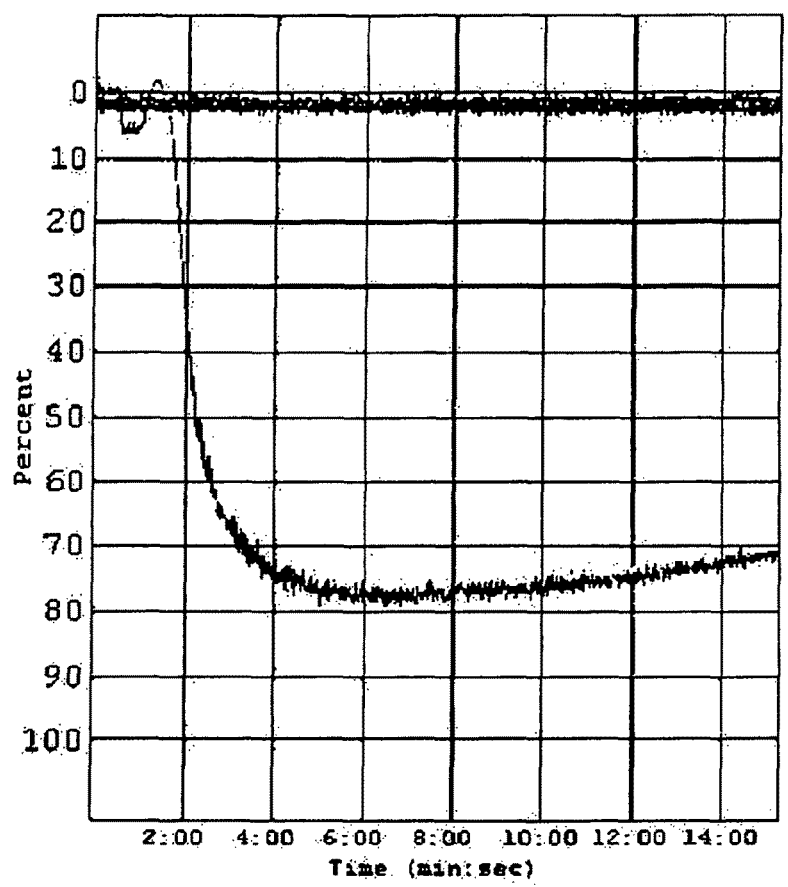

FIG. 11. Effect of scFv 9O12.2 on platelet aggregation induced by collagen. Washed human platelets ($2.10^8$ mL) were incubated with an irrelevant scFv (bottom curve), Fab 9O12.2 (25 µg/ml) (upper curve), isolated monomeric scFv 9O12.2 (black) for 5 min at 37° C. and the collagen was added. Aggregation was analyzed at 37° C. with stirring conditions and change in light transmission was recorded.

Figure 12:
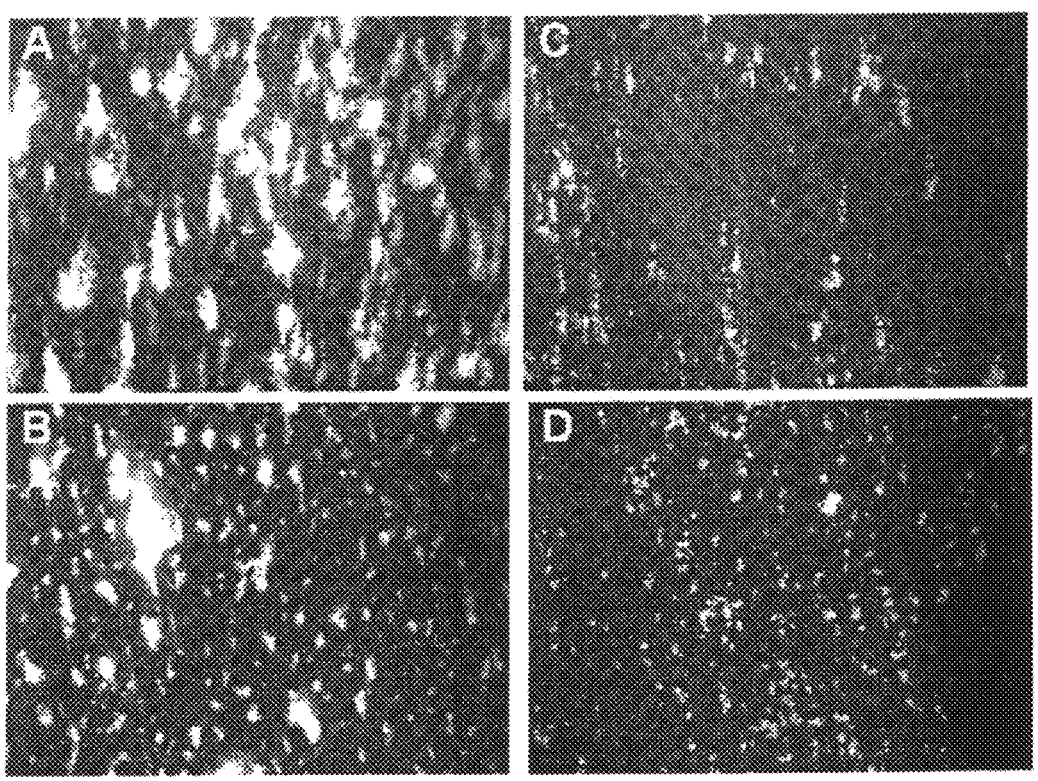

FIG. 12. Effect of $_m$scFv 9O12 on platelet aggregation induced by collagen under arterial flow conditions. Whole blood (5 mL) was labeled with the cell permeable fluorochrome DIOC-6 platelets appear in white on the picture was incubated with PBS (A) or antibody fragments at 50 µg.mL$^{-1}$ (B-D), and then perfused onto collagen-coated coverslips in a flow-chamber at 1 500 s'. The formation of platelet aggregates bound to the collagen matrix was recorded with a fluorescent microscope. (B) irrelevant scFv 9C2. (C) mscFv9O12. (D) Fab 9O12.

Figure 13:
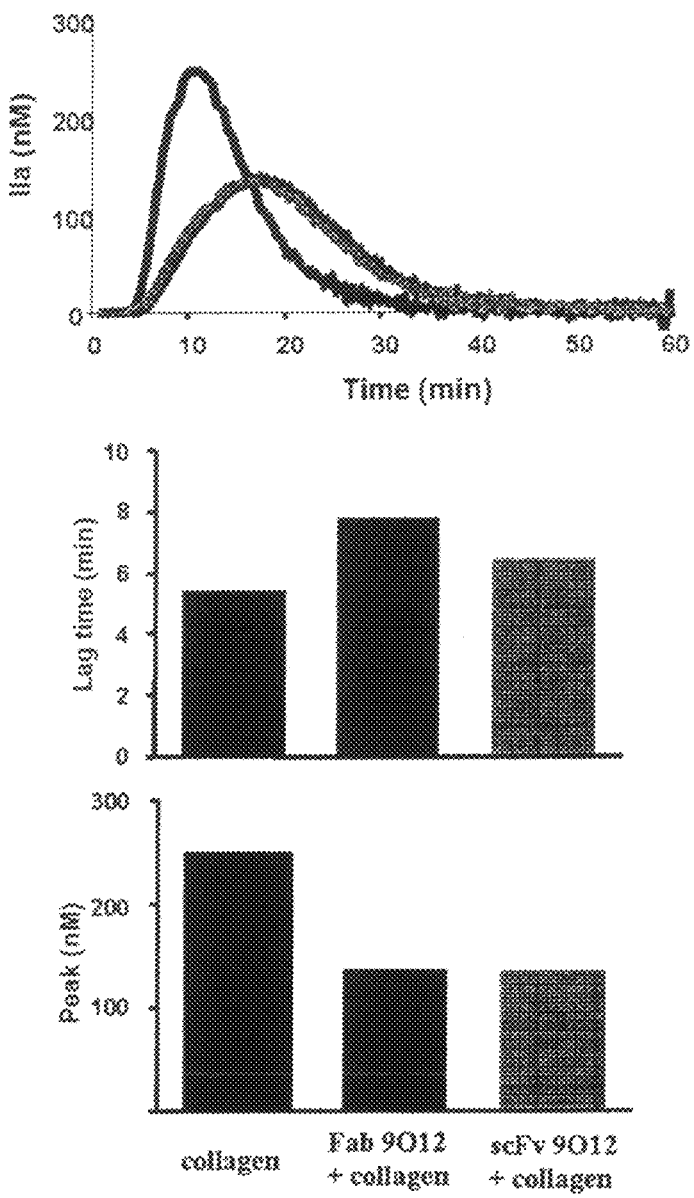

FIG. 13 Effect of mscFv 9O12 on thrombin generation induced by collagen in PRP. Platelet rich plasma (PRP) was preincubated with vehicle (black curve) or 50 µg.mL$^{-1}$ of Fab9O12 (dark gray) or $_m$scFv 9O12 (light gray) before adding collagen (5 µg.mL$^{-1}$). Thrombin generation was initiated by adding 0.5 pM tissue factor and 16.6 mM CaCl$_2$. Thrombin concentration was determined using a fluorescent substrate and was calculated relative to a calibrator. The traces are from one representative experiment. Bars graphs represent mean±SD of the lag phase and the peak values (n=3) (The bars corresponding to the SD are too small to be visible).

FIG. 14. Nucleotide sequence and deduced amino acid sequence of humanized VH and VL domains and of the first humanized 9O12.2 scFv fragment (hscFv 9O12.2(1)). A. Humanized 9O12.2 VII (1) nucleotides (SEQ ID NO: 31) and amino acids (SEQ ID NO:26) are displayed. B. Humanized 9O12.2 VL (1) nucleotides (SEQ ID NO: 32) and amino acids (SEQ ID NO:27) are displayed. C. Humanized hscFv9O12.2 (1) nucleotides (SEQ ID NO:30) and amino acids (SEQ ID NO:28) are displayed.

FIG. 15. Characterization of the first humanized scFv 9O12.2(hscFv 9O12.2(1)). Affinity binding to GPVI sepharose: The periplasmic fraction of recombinant bacteria was loaded onto a GPVI sepharose column. Retained proteins were analyzed by Western-Blot using an anti-c-myc IgG followed by anti-mouse antibody coupled to HRP and ECL revelation. A single band is detected with a molecular mass of 28.5 kDa as expected for the humanized scFv.

Figure 16:
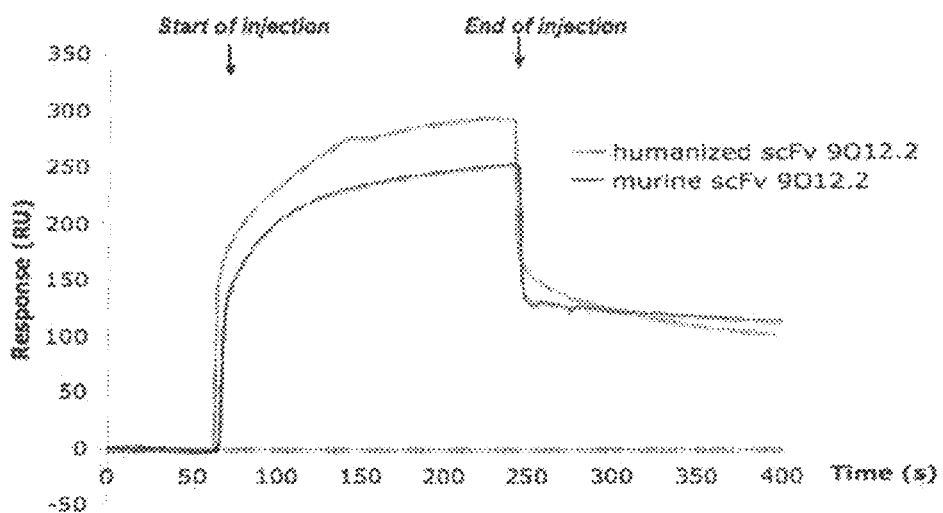

FIG. 16. Binding of scFv 9O12.2 to GPVI-Fc. Purified first humanized scFv (hscFv 9O12/(1), dark grey) and mscFv (light grey) were injected on GPVI-Fc immobilized on a CM5 sensorchip. Sensorgrams are shown after deduction of the blank signal.

Figure 17:
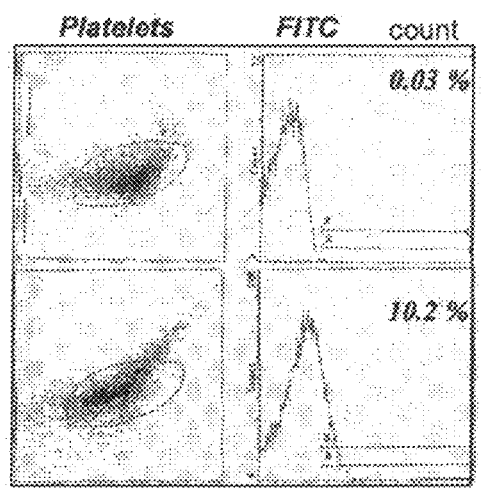

FIG. 17. Binding of the first humanized scFv9O12 (hscFv 9O12.2 (1)) to human platelets. Human platelets were incubated with bacterial periplasmic extracts. scFv bound to platelets was detected using FITC coupled anti-c-myc antibody. Binding to platelet was analyzed on XL Epics Coulter Flow cytometer. An irrelevant scFv was used as a negative control (upper panel). The shift to the right of the histogram (lower panel) indicates that the humanized scFv 9O12.2 binds to platelet GPVI.

Figures 18A, 18B:
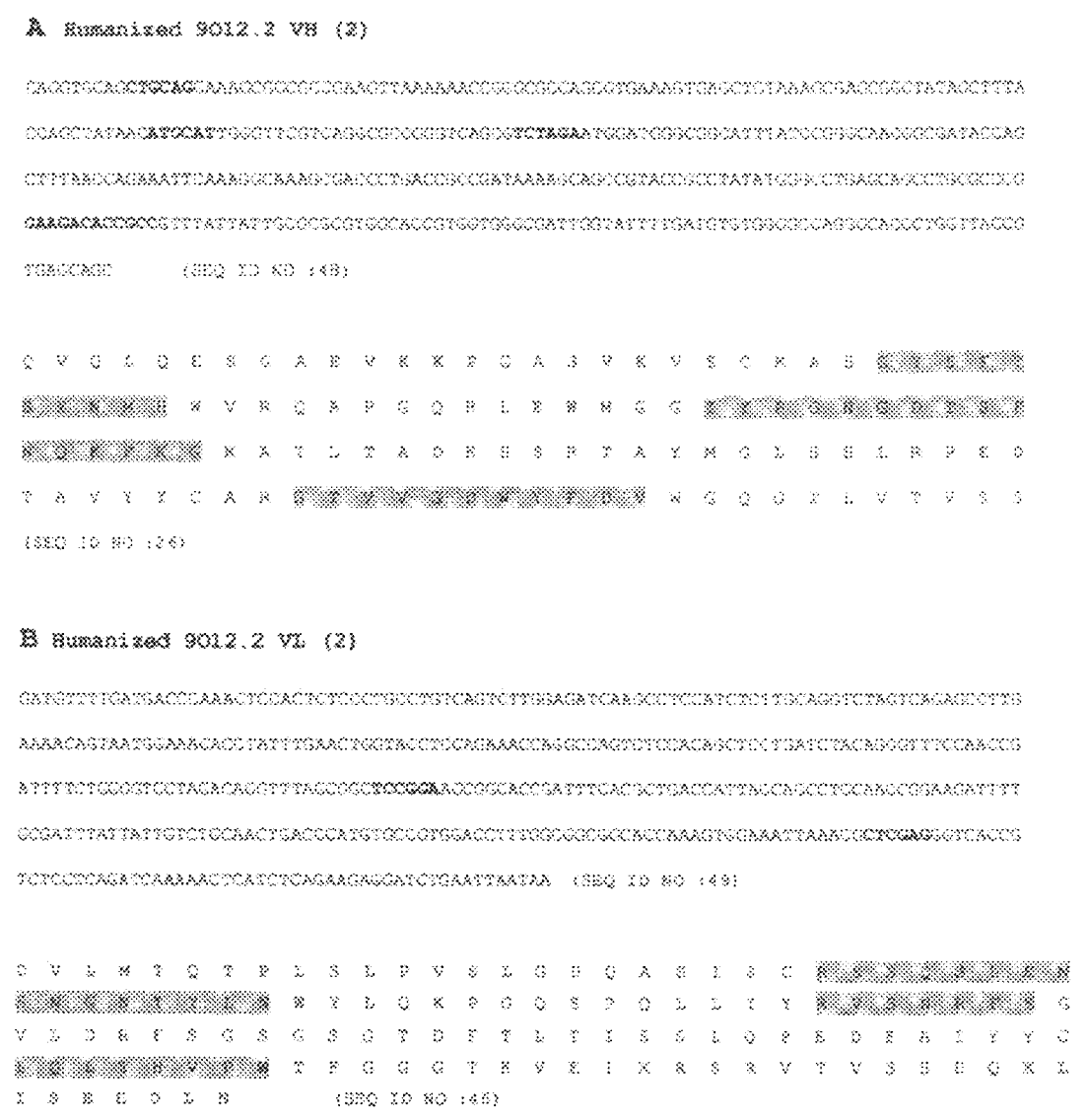
Figure 18C:
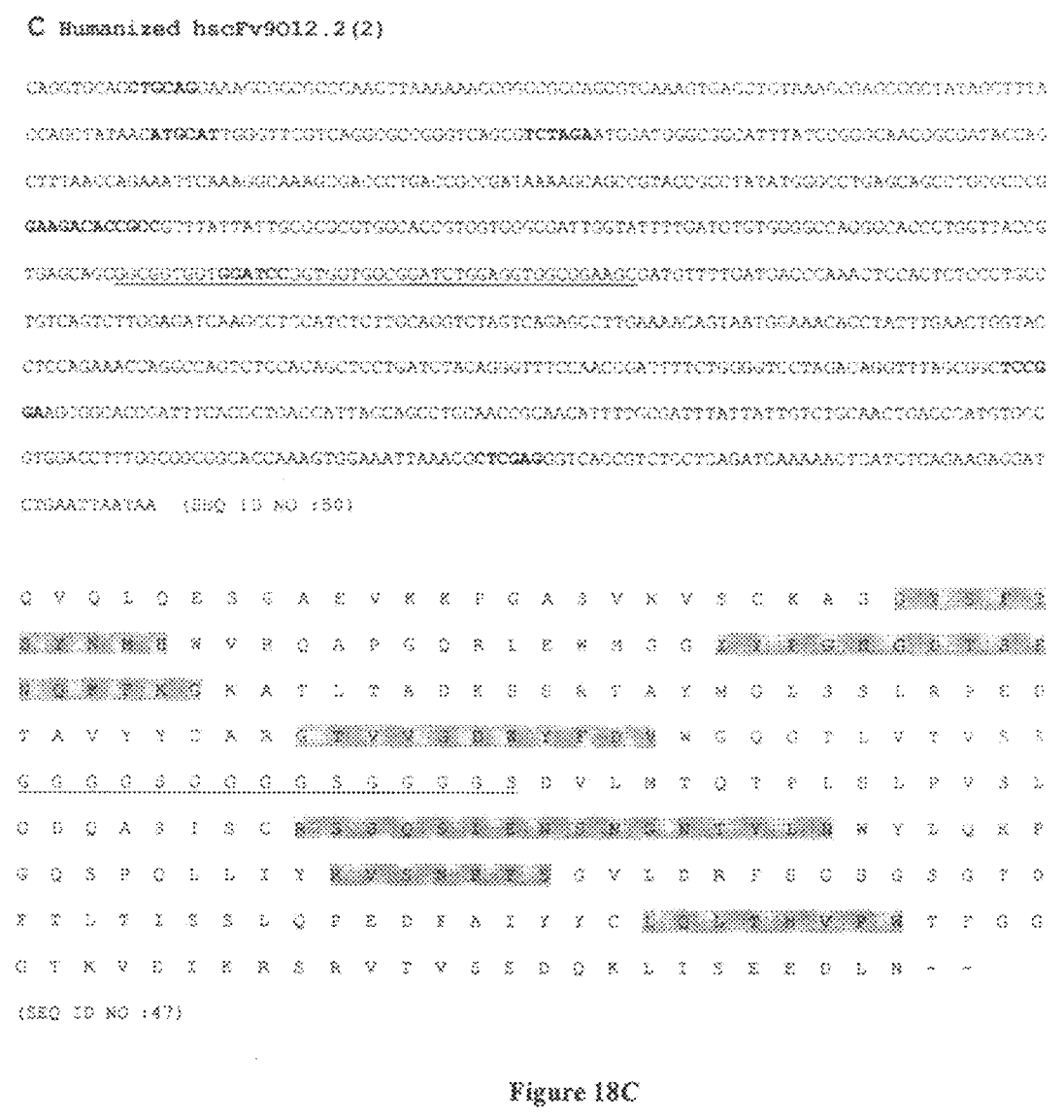

FIG. 18. Nucleotide sequence and deduced amino acid sequence of humanized VII and VL domains and of the second optimized humanized 9O12.2 scFv fragment (hscFv 9O12.2(2)). A. Humanized 9O12.2 VH (2) nucleotides (SEQ ID NO: 48) and amino acids (SEQ ID NO:26) are displayed. B. Humanized 9O12.2 VL (2) nucleotides (SEQ ID NO: 49) and amino acids (SEQ ID NO:46) are displayed. C. Humanized hscFv9O12.2(2)) nucleotides (SEQ ID NO:50) and amino acids (SEQ ID NO:47) are displayed. Enzymes restriction sites are in bold. The linker between VH and VL domains is underlined. CDR regions are highlighted in grey.

Figure 19:
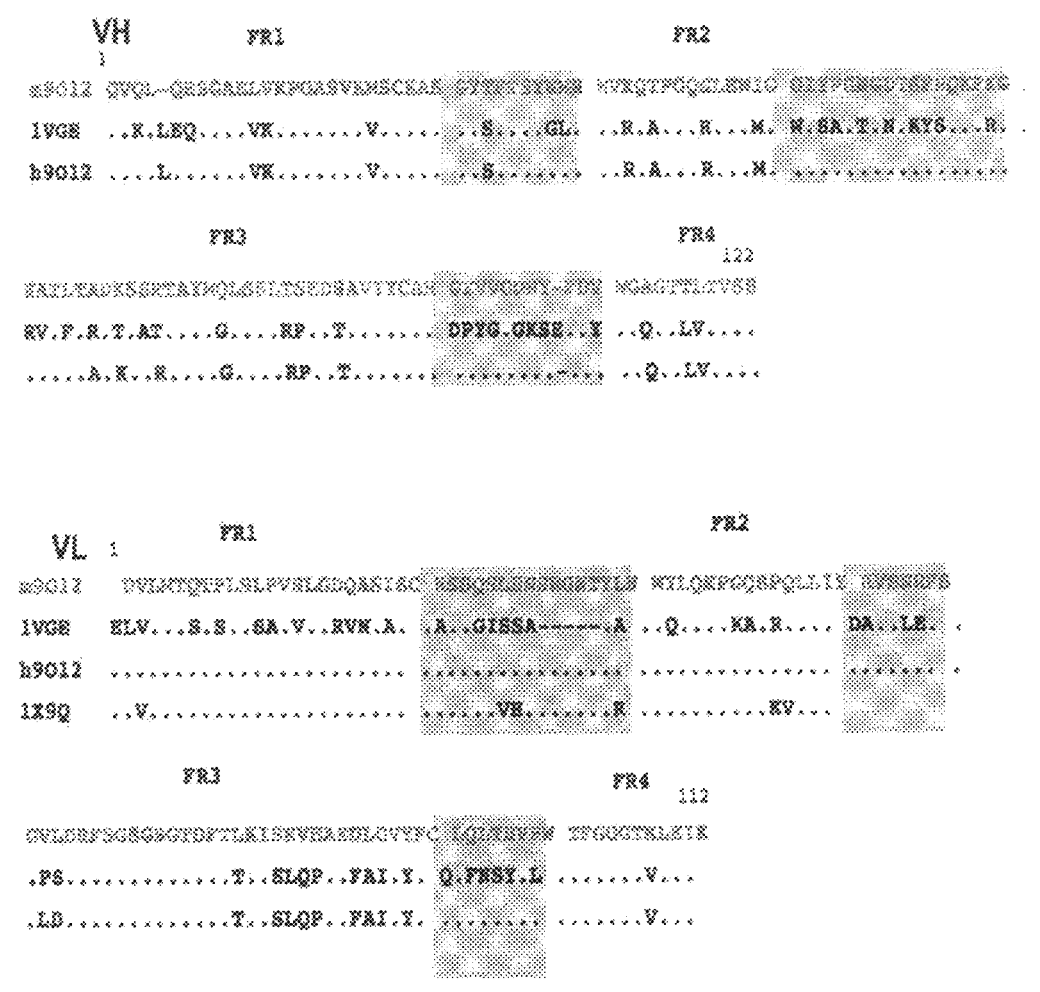

FIG. 19. Optimized humanization of the 9O12 antibody variable domains. Sequence analysis of antibody V-domains: murine 9O12 (m9O12; VH is SEQ ID NO:26, VL is SEQ ID NO:27); 1VGE (VH is SEQ ID N0:52, VL is SEQ ID NO:53): humanized 9O12 (h9O12; VH is AA 1-120 of SEQ ID NO:47, VL is AA 136-247 of SEQ ID NO:47)) and 1×9Q (VL is SEQ ID NO: 51). (.) indicates residues identical to murine 9O12. (-) indicates a gap. Residues of the humanized V-domains having no similarity with murine 9O12 are shown in red and blue (residues $A_{H71}$, $K_{H73}$, $R_{H76}$, $L_{L59}$, $D_{L60}$ according to the Kabbat nomenclature). CDRs are highlighted in gray.

FIG. 20. Characterization of the second humanized (hscFv 9O12.2 (2). A—Western-blot detection of recombinant scFvs using the anti-cMyc antibody. B—Flow cytometry analysis. Human platelets were pre-incubated with antibody fragments for 30 minutes. scFvs binding was detected using FITC conjugated anti-c-Myc antibody

EXAMPLES

Example 1

Synthesis and Activity of a Murine and a First Humanized Single Chain Variable Fragment scFv 9O12.2 Directed Against Human Glycoprotein VI 1.1 Experimental Procedure
1.1.1 Material
Media and Solutions LB (Luria-Bertani), DIFCO 402-17; LB-Agar, DIFCO 445-17; 2×TY (Trypton-Yeast), DIFCO 244020; TES: Tris-HCl 30 mM, EDTA 1 mM, sucrose 20%, pH 8.5; PBS: NaCl 0,14 M, KCl 13 mM, KH$_2$PO$_4$ 9 mM, Na$_2$HPO$_4$ 50 mM, pH 7.4; BBS: boric acid 50 mM, NaCl 150 mM, pH 7.6; Ampicillin, Euromedex EU-0400C; Isopropyl β-D-thiogalactoside (IPTG), Euromedex EU0008-B; Bovine serum albumin (BSA), Sigma B4287; FITC-coupled anti-c-myc IgG, Sigma F-2047; desoxyribonuclease A, aprotinin: Sigma A-6279; HRP-coupled anti-c-myc IgG, Invitrogen R951-25; orthophenyl diamine (OPD): Sigma P8787, Trizol: Invitrogen, Collagen Horm type I: Nycomed, pGEM$_T$ cloning vector, Promega. The pSW1 plasmid was used for scFv expression. 6H8 and 9C2 was used as non relevant scFv.

Oligodesoxyribonucleotides Sequences

The used oligodesoxyribonucleotides are listed in the following Table 2:

TABLE 2

Oligodesoxyribonucleotides

| Name | 5'-3' sequence | SEQ ID NO |
|---|---|---|
| T7 | TAATACGACTCACTAGGGCGAAT | SEQ ID NO: 33 |
| pSWRev | CGGCAGCCGCTGGATTGTTA | SEQ ID NO: 34 |
| pSWFor | CGAGCTTAGCCCTTATAATTCAG ATCCTC | SEQ ID NO: 35 |
| Link9O1-2VLRev | GGAGGCGGATCCGGTGGTGGCGG ATCTGGAGGTGGCGGAAGCGATG TTTTGATGACCCAAACTCCACT | SEQ ID NO: 36 |
| Link9O1-2VHFor | ACCACCGGATCCGCCTCCGCCTGA GGAGACGGTGACCGT | SEQ ID NO: 37 |
| 9O12.2-mycFor | GACCCTCGAGCGTTTGATCTCCAG CTTGGT | SEQ ID NO: 38 |
| 9O12.2-H3Rev | GGCGACTGGTACTTCGATGTC | SEQ ID NO: 39 |
| 9O12.2-H2Rev | AAATGGTGACACTTCCTTCAATCA | SEQ ID NO: 40 |
| 9O12.2-L1For | GTTTTCAAGGCTCTGACTAGACCT | SEQ ID NO: 41 |
| MKC5For | GGATTACAGTTGGTGCAGCATC | SEQ ID NO: 42 |
| MKRevU | GAYATTGTGMTSACMCARWCT | SEQ ID NO: 43 |
| VHFor | CGGGATCCTCTAGACAGTGGATAR ACMGATGG | SEQ ID NO: 44 |
| VHRev | CGGGATCCTCTAGAGGTSMARCT GCAGSAGTCWGG | SEQ ID NO: 45 |

Preparation of Human Platelets

Human platelets were prepared as previously described (9)

Flow Cytometry

"Simple FITC labelling of platelets program" flow cytometer Coulter Epics XL was used Preparation of GPVI-Sepharose:

Reagents: CnBr-sepharose was from Amersham-Pharmacia. Recombinant soluble GPVI (GPVI-Fc) was produced and purified in the laboratory (9).

Method: CnBr-sepharose (Amersham-Pharmacia) was prepared as indicated by the supplier. It was incubated with GPVI-Fc (8 mg/mL of gel in NaHCO$_3$ 0.1 M; NaCl 0.5 M pH 8.3) for 18H under agitation. The gel was filtered and the protein concentration in the filtrate was measured to determine the yield of the coupling. After a blocking step with ethanolamine (1 M, pH 8.8) for two hours at room temperature in the dark with gentle stirring, the gel was filtered and washed successively with the coupling buffer and with sodium acetate 0.1 M, NaCl 0.5 M pH 4. The gel was stored at 4° C. in PBS containing sodium azide (1%).

1.1.2 Procedures

Genetic Construction of scFv 9O12.2:

mRNA was isolated from freshly subcloned hybridoma 9O12.2.2 cells which produce the immunoglobulin G (IgG) 9O12.2.2 directed against human GPVI. cDNA encoding the antibody variable domains were cloned after RT-PCR and the scFv 9O12.2 gene was created by PCR splicing with overlap extensions. An expression vector derived from pUC 19 [pSW I vector (37)] was used for the production of the scFv 9O12.

It contains the LacZ promotor inducible with IPTG, the pelB leader sequence and, downstream, the gene coding for the scFv 9O12.2 fused to the flag c-myc and a gene of resistance to ampicillin used to select the recombinant bacteria.

Figure 1:
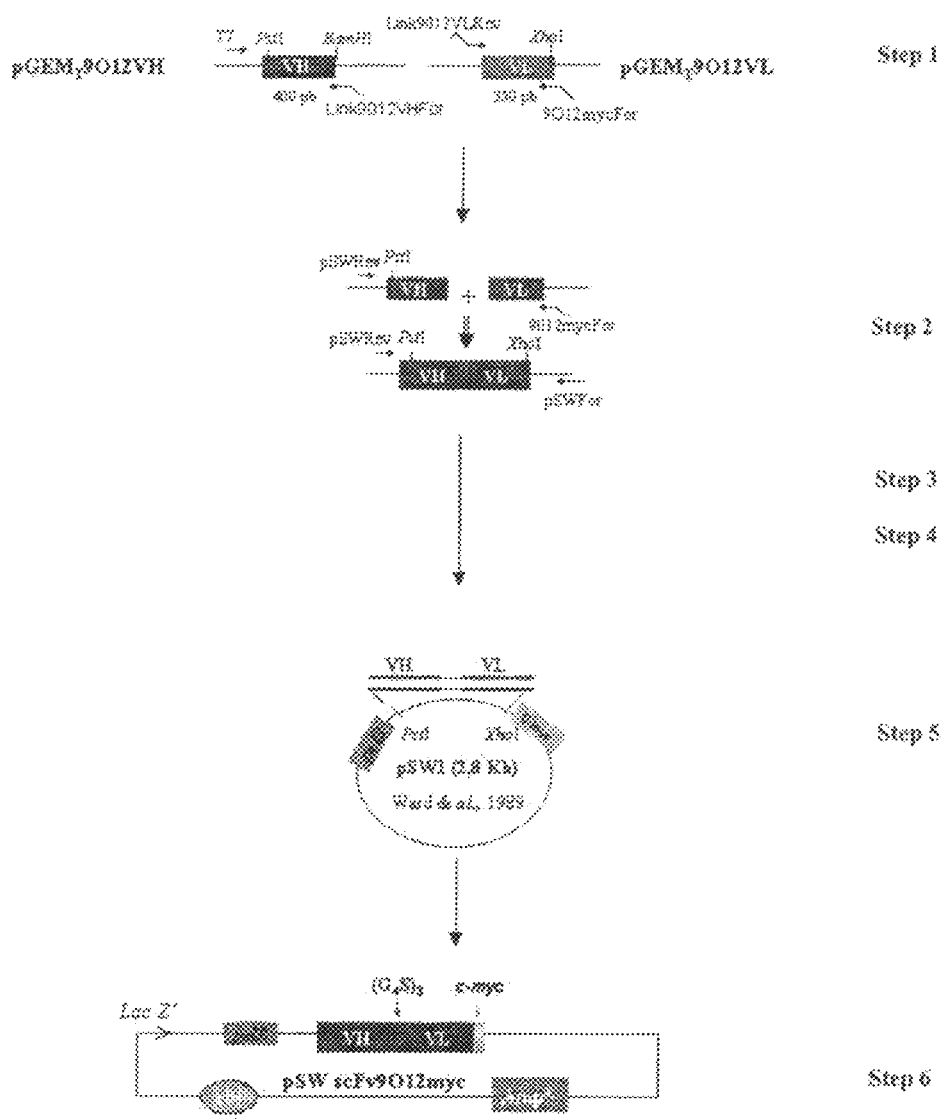
FIG. 1. Schematic description of the method used to construct scFv 9O12.2 expression vector. Step 1: PCR amplification 9O12.2.2 monoclonal antibody VH segment using T7 and Link9O12.2VHFor primers and VL segment using Link9O12.2VLRev and 9O12.2mycFor primers. Step 2: Overlap PCR amplification using pSWRev and 9O12.2mycFor primers followed by PCR amplification using pSWRev and pSWFor primers, thus generating a nucleic acid coding scFv 9O12.2. Step 3: DNA purification of PCR products. Step 4: Digestion of purified DNA using Pst1 and Xho1 restriction enzymes. Step 5: Cloning of the digested product into pSW1 expression vector. Step 6: Sequencing of the obtained construction.

The method used to construct the scFv 9O12.2 expression vector is summarized in FIG. 1.

Production of the scFv 9O12.2

The leader sequence pelB allows the recombinant scFv 9O12.2 to be addressed to the periplasm of bacteria transformed with the expression vector pSW scFv 9O12.2myc. The bacteria Topp1® (non K12, Rif$^r$, F', proAB, lacI$^q$ZΔM15, Tn10, tet$^r$) (Stratagene, La Jolla, USA), colony 55T1 is used to produce the scFv 9O12.2.

J0: Plating of the 55T1 colony on LB-Agar supplemented with ampicillin (sub-cloning). Incubation overnight at 37° C.

J1: 4 PM: Selection of one clone and culture in 5 mL LB supplemented with ampicillin. Incubation overnight at 37° C. with agitation (125 rpm).

J2: 8 AM: Measurement of the absorbance at 600 nm (expected value $A_{600nm}$=1.5±0.1). Transfer of 4 mL to 500 mL 2×TY+Ampicillin. Incubation at 37° C. with agitation (125 rpm) until $A_{600nm}$ reaches 1.5±0.1 (~8 H). Then, induction of the bacteria with 0.8 mM IPTG. Incubation for 16 H at 16° C. with agitation (75 rpm).

J3: periplasmic proteins extraction: Bacterial cells are collected by centrifugation (3600 g, 20 min at 4° C.). Pellet is gently resuspended in 10 mL TES buffer and incubated for 30 min on ice. The cells are then subjected to a mild osmotic shock by addition of TES buffer, diluted 1:4. After incubation on ice for 30 min., insoluble material is removed by centrifugation at 15 000 g for 30 min at 4° C. Then deoxyribonuclease A (50 U) and proteases inhibitor (Aprotinin 2 μg/mL) are added to the supernatant corresponding to the periplasmic proteins extract. After that, the preparation is extensively dialysed against PBS at 4° C. A periplasmic proteins extract of bacteria expressing an irrelevant scFv is prepared according to the same procedure.

J4: Centrifugation at 15 000 g for 30 min at 4° C. The supernatant is collected and its absorbance at 280 nm measured (expected value: 1.5 to 3.0). One sample is taken for analysis and the preparation (~35 mL±2.0) is stored at −20° C.

J5: Screening of the periplasm extracts by flow cytometry: washed human platelets (2×10$^7$/mL) are incubated with 100 μL of periplasmic proteins extract for 30 min at room temperature. The FITC-coupled anti-c-myc IgG is added and the incubation continued for 30 min at room temperature in the dark. A negative control is performed with the anti-c-myc antibody in the absence of periplasm extracts. Samples are analysed by flow cytometry (Coulter Epics XL).

J6: Purification of the scFv 9O12.2 by affinity chromatography on GPVI-coupled sepharose. The periplasm extract (35 mL) is incubated with 500 μL GPVI-Sepharose for 12H at 4° C. and 4H at room temperature. The mixture is loaded on a column. The flow-through fraction is collected before washing with PBS until $A_{280nm}$=0.001; Elution is performed with Glycine 0.1 M pH 3.0 and fractions of 400 μL are collected in tubes containing 5 μL Tris 3 M on ice. $A_{280nm}$ is measured and fractions with $A_{280nm}$ higher than 0.2 are pooled and extensively dialysed against PBS.

J7: The sample is centrifuged at 15000 g for 30 min. Protein concentration is determined after measuring $A_{280nm}$.

The ProtParam software is used to determine the theorical Mr of the scFv9O12.2myc and its extinction coefficient at 280 nm.

Protein Analysis:

Protein analysis was made by electrophoresis in polyacrylamide slab gels in the presence of SDS according to Laemmli; by immunoblotting after transfer of the proteins to nitrocellulose, incubation with an HRP coupled anti-c-myc antibody and detection using 4 chloro-naphtol.

Experimental Determination of the Mass

Mr of purified scFv is determined on a matrix-assisted laser desorption/ionization time-of-flight (MALDI-TOF) mass spectrometer (Voyager DE-PRO; PerSeptive Biosystems Inc., Framingham, Mass.). The saturated solution of α-cyano-4-hydroxycinnamic acid in 50% acetonitrile and 0.1% TFA is used as matrix and the spectrometer is calibrated using external standard peptide mixtures.

Size Exclusion-Diffusion Chromatography:

Purified scFv preparation were resolved by size-exclusion diffusion chromatography on a Superdex 75 HR column calibrated with standards of known molecular mass. 200 μL of sample was injected with a rate of 0.5 mL/min. Detection is monitored using UV detector at 226 nm. Fractions were used immediately for analysis.

Binding to Soluble Recombinant GPVI

Microtiter plates are coated with GPVI-Fc (10 μg/mL, 100 μL per well) overnight at 4° C. Wells are saturated with 100 μL BSA for 2 hours at room temperature. Then, increasing concentrations of scFv 9O12 are added to the wells for 2 hours. Bound scFvs are detected after incubation for 2 h at room temperature with HRP-coupled anti-c-myc-antibody (1/750 en PBS). Then, the substrate solution (OPD) is added to the wells for 5 min. and absorbance is read at 492 nm. Two controls are performed: the first one using an irrelevant scFv in place of scFv 9O12.2 and the second one by omitting coating with GPVI-Fc. Five washes with PBS containing 0.05% Tween and 0.1 mg/mL BSA are carried out between each intermediate step.

Construction of the First Humanized scFv Fragment (hscFv 9O12.2(1))

The approach to humanize the scFv 9O12.2 has been adapted from CDR grafting technology 9. The CDRs of murine 9O12.2 antibody have been grafted on a human variable-chain framework. The choice of the human antibody has been done using the following criteria: the crystallographic structure has been elucidated (1 VGE in pdb library); the variable domains of the human antibody 1VGE present a high degree of sequence homology with the variable domains of 9O12.2 (VH 60,6%; VL 55,4%); Structure comparison of the crystallographic data of the candidate human antibody 1 VGE and the model of the variable domains of 9O12.2 was done and allowed us to validate the choice of the human acceptor scaffold 1VGE. This strategy minimizes the risk of lowering the stability of the interaction between VH and VL domains while preserving the scaffold required for correct folding of the CDR, preserving a high affinity for the antigen. The human antibody 1VGE selected based on these analysis allowed us to construct the humanized 9O12.2 scFv. The nucleotide sequence encoding the humanized scFv 9O12.2 was optimized. First, restriction sites between CDR regions were introduced to make possible adjustments for optimal binding characteristics. Optimization was then performed using the bacterial codon usage in order to express the humanized scFv in the procaryotic expression system *E. coli*.

More precisely, we first constructed a 3D-structural model of $_m$scFv9O12 in silico after identifying the crystal structures with sequences most similar to the 9O12 variable domains.

All these sequences were of murine origin. The top four scoring structures of murine origin were used for modeling. For the VH gene, we used 1PLG, 1MNU, 1A5F and MI which have 66-78% sequence identity (79-85% similarity) with 9O12. For the VL gene, we used 1PLG, 1IGI, 1MNU and 1AXT, which have 87-90% sequence identity (94-95% similarity). The 3D structures of all these sequences were solved with a resolution higher than 2.8 Å. Twenty models were generated for each domain using Modeler 3.0 software, and the best one was selected on the basis of the RMSD value (0.13 Å for VH and 0.703 Å for VL) and detailed inspection.

We then proceeded to the humanization of 9O12 V-domains. To do this, FASTA searches were performed to independently align VH and VL amino acid sequences against a repertoire of human antibody sequences registered in the PDB data bank. Among the human V-domains that matched 9O12 we first selected a VH and a VL from the same antibody molecule in order to preserve the interdomain contacts that occur in a natural antibody. The human antibody 1VGE was selected because it had the best identity score with 9O12 when the entire V-domain sequences were spanned, and found to exhibit 62% and 55% identity for VH and VL, respectively. When calculated over framework region sequences alone, the identity was even slightly better, showing 69.5% and 65.4% identity, respectively. In addition, the crystallographic structure of 1 VGE was solved at high resolution (2 Å and R value 0.18). We therefore decided to graft 9O12 CDRs onto the 1 VGE template in silico. A gene encoding this construct was chemically synthesized and inserted into pSWI exactly as had been done for $_m$scFv9O12. TOPPI cells transformed with this vector were induced to express the recombinant protein.

This resulted in a first humanized scFv fragment named hscFv 9O12.2(1)

Competition with 9O12.2 IgG:

The scFv9O12.2 (100 μg/ml) was mixed with increasing concentrations of 9O12.2 IgG before addition to GVI-Fc coated microtitration wells. Bound scFv was detected as above.

Effect of the Antibody on GPVI Binding to Collagen:

Microtitration wells are coated with fibrilar type I collagen (Collagen Horn, Nycomed, Munich 2 μg/well), saturated with BSA and washed. Increasing amounts of GPVI-Fc pre-incubated with PBS, scFv 9O12.2 or Fab 9O12.2 are added to the wells. After one hour at room temperature and washing bound GPVI-Fc is detected using a peroxydase-coupled anti-human Fc and OPD.

Surface Plasmon Resonance (SPR, BIAcore):

Binding of the anti-GPVI scFv to recombinant GPVI-Fc is analyzed with surface plasmon resonance using a BIAcore 2000 system (Uppsala, Sweden). Binding studies is performed with scFv 9O12, Proteolytic Fab and parental IgG.

Recombinant GPVI-Fc is immobilized (~600 RU) onto a Carboxy-Methyl Dextran CM5 sensor chip using the amine coupling method (Wizard procedure). Antibody is then passed over the immobilized recombinant GPVI-Fc in HBS-EP buffer (0.01 M HEPES pH 7.4, 0.15 M NaCl, 0.005% polysorbate 20 (v/v)) at a flow rate of 20 μl/min at 25° C. Kinetic constants ($k_a$, $k_d$) and affinity are determined using BIAevaluation version 3.1 software, by fitting data to binding model. HBS-EP is the running buffer. 10 mM glycine-HCl pH 2.5 injected for 30 s at 20 μl/min is the regeneration buffer. All reagents and buffers used are from Biacore.

Binding of the Purified scFv to Human Platelet GPVI

Washed human platelets ($2.10^7$/mL) are incubated for 30 minutes at room temperature with 0 to 100 μg/ml of purified scFv 9O12 and then incubated again for 30 minutes at room temperature in the dark with 5 μL of FITC coupled anti-c-myc IgG (dilution 1:60). Cell fluorescence is measured using a flow cytometer (Epics XL, Coulter). Background is determined by using an irrelevant scFv in place of scFv 9O12.2.

Platelet Aggregation

Washed human platelets ($3 \times 10^8$/mL) are preincubated for 5 min at 37° C. without stirring with PBS, the scFv 9O12.2 or the Fab 9O12.2. Aggregation is initiated by adding type I collagen and the changes in light transmission is continuously recorded (Chronolog Aggregometer).

Platelet Aggregation Under Flow Conditions

Platelet adhesion to collagen under flow conditions was measured essentially as described elsewhere (9). Glass coverslips were coated with fibrillar type I collagen (50 μg. $mL^{-1}$). Blood from healthy volunteers was collected on 40 μM PPACK, and labelled with DIOC-6 (1 μM). Blood aliquots were incubated for 15 minutes at room temperature with buffer or purified antibody fragment (Fab 9O12, $_m$scFv9O12, scFv 9C2) at a final concentration of 50 μg.$mL^{-1}$. The mixture was then perfused over the collagen-coated coverslips inserted in a flow-chamber at 1500 $s^{-1}$ for 5 minutes. Transmission and fluorescent images were recorded in real time using a fluorescent microscope. Fluorescent images were obtained from at least ten different collagen-containing microscopic fields which were arbitrary chosen at the end of perfusion. Area coverage of fluorescent images was analyzed off-line using Histolab software (Microvision, Evry, France).

Thrombin Generation

Thrombin generation was continuously measured in platelet rich plasma (PRP) using the thrombogram method as previously described (38). Briefly, citrated PRP ($1.5 \times 10^8$ platelets $mL^{-1}$) was incubated with the antibody fragments for 10 min at 37° before adding the collagen. Ten minutes later, thrombin generation was initiated by transferring the samples into the wells of a microtitration plate containing tissue factor (0.5 pM). After 5 min at 37° C., the reaction was initiated by adding buffer containing $CaCl_2$ and the fluorescent thrombin substrate Z-GGR-AMC (Stago, Asnières, France)). Fluorescence accumulation of the cleaved substrate was continuously measured at excitation and emission wavelengths of 390 and 460 nm respectively. First derivative curves of fluorescence accumulation were converted into thrombin concentration curves using a thrombin calibrator (39). The peak height is an indicator of the maximum rate of thrombin formation, and is sensitive to platelet activation.

1.2 RESULTS 1.2.1 Murine 9O12.2 scFv (mscFv 9O12.2)

Cloning of Antibody 9O12.2.2 VH and VL cDNAs 9O12.2 is a murine $IgG_1$ (kappa chain). Total RNA was extracted from about $5.10^8$ freshly subcloned hybridoma cells in a single-step procedure using Trizol. This RNA preparation was used as a template for first-strand cDNA synthesis. Double strand cDNAs encoding IgG 9O12.2.2 VH and VL domains were then amplified by PCR using primers sets (VHRev, VHFor) and (MKRevU, MKC5For) respectively. VH cDNA sequence was unique and this was confirmed by sequencing of the cDNA after cloning into pGEMT. The sequence of the PCR product corresponding to the VL domain was scrambled. After cloning into pGEMT and sequencing of several clones, two VL sequences were identified. Data analysis using fasta analysis showed that one of the VL sequence derived from the MOPC-21 clone that express an endogenous and aberrant non-functional Vk mRNA (Gene bank acc number M35669). The nucleotide and deduced amino acid sequences of the other VL gene and the VH gene are shown in FIG. 2 as part of the scFv 9O12.2. These sequences were compared with immunoglobulin variable region sequences registered in several data banks (UNIPROT UNIREF100 UNIREF90 UNIREF50 UNIPARC SWISSPROT IPI PRINTS SGT PDB IMGTHLAP, PATENT: epop jpop uspop). (DNA banks: EMBL, HUMAN, MOUSE, SYNTHETIC, PATENT). This allowed us to identify the three loops corresponding to the complementary determining regions of the VH and VL regions and the amino-acids residues involved in the canonical structures.

CDRs were identified according to the following rules as deduced from Kabat et al. (1991) and Chotia and Lesk (1987):

CDR-L1:
  Start—Approx residue 24
  Residue before is always a Cys
  Residue after is always a Trp. Typically TRP-TYR-GLN, but also, TRP-LEU-GLN, TRP-PHE-GLN, TRP-TYR-LEU
  Length 10 to 17 residues CDR-L2:
  Start—always 16 residues after the end of L1
  Residues before generally ILE-TYR, but also, VAL-TYR, ILE-LYS, ILE-PHE
  Length always 7 residues.

CDR-L3:
  Start—always 33 residues after end of L2
  Residue before is always Cys
  Residues after always PHE-GLY-XXX-GLY
  Length 7 to 11 residues CDR-H1:
  Start—Approx residue 26 (always 4 after a CYS) [Chothia/AbM definition] Kabat definition starts 5 residues later
  Residues before always CYS-XXX-XXX-XXX
  Residues after always a TRP. Typically TRP-VAL, but also, TRP-ILE, TRP-ALA
  Length 10 to 12 residues (AbM definition) Chothia definition excludes the last 4 residues CDR-H2:
  Start—always 15 residues after the end of Kabat/AbM definition) of CDR-H1
  Residues before typically LEU-GLU-TRP-ILE-GLY, but a number of variations
  Residues after LYS/ARG-LEU/ILE/VAL/PHE/THR/ALA-THR/SER/ILE/ALA
  Length Kabat definition 16 to 19 residues (AbM definition ends 7 residues earlier)

CDR-H3:
  Start—always 33 residues after end of CDR-H2 (always 2 after a CYS)
  Residues before always CYS-XXX-XXX (typically CYS-ALA-ARG)
  Residues after always TRP-GLY-XXX-GLY
  Length 3 to 25 residues The VH cDNA sequence showed 92.96% identity with the cDNA encoding another murine VH domain (MMMD52C). For the VL we found 98.51% identity with the cDNA sequence encoding the VL domain of murine anti-acetyl-Lys (BD174891). The deduced amino acid sequences analysis also showed high homology with the sequence of murine Ig. 9O12.2 VH showed 89.256% identity with the deduced amino-acid sequence of an anti-CD20 murine IgG (BD688655). 9O12.2 VL showed 96.43% identity with the deduced amino-acid sequence of an anti-acetyl Lys murine IgG (BD581288).

Design of the scFv 9O12.2

The nucleotide and deduced amino acid sequences of the scFv 9O12.2 is shown in FIG. 2. The scFv is 266 amino acids long and is composed of the VH and VL sequences linked together by a $[G_4S]_3$ linker and followed by a short spacer (8 residues) and the c-myc flag sequence (11 residues).

Theoretical Structural Characteristics of the scFv

The theoretical molecular mass of the scFv is of 28393.5 as determined using ProtParam software. Its pI is 6.92 and its extinction coefficient 49640 $M^{-1}$ $cm^{-1}$ at 280 nm (Table 3).

TABLE 3

Theoretical structural characteristics of scFv 9O12 as deduced from bioinformatic analysis using ProtParam software Number of amino acids: 266
Molecular weight: 28393.5
Theoretical pI: 8.82
Amino acid composition:

| | | |
|---|---|---|
| Ala (A) | 11 | 4.1% |
| Arg (R) | 9 | 3.4% |
| Asn (N) | 9 | 3.4% |
| Asp (D) | 11 | 4.1% |
| Cys (C) | 4 | 1.5% |
| Gln (Q) | 15 | 5.6% |
| Glu (E) | 11 | 4.1% |
| Gly (G) | 37 | 13.9% |
| His (H) | 2 | 0.8% |
| Ile (I) | 7 | 2.6% |
| Leu (L) | 24 | 9.0% |
| Lys (K) | 13 | 4.9% |
| Met (M) | 4 | 1.5% |
| Phe (F) | 9 | 3.4% |
| Pro (P) | 8 | 3.0% |
| Ser (S) | 36 | 13.5% |
| Thr (T) | 21 | 7.9% |
| Trp (W) | 6 | 2.3% |
| Tyr (Y) | 11 | 4.1% |
| Val (V) | 18 | 6.8% |

Total number of negatively charged residues (Asp + Glu): 22
Total number of positively charged residues (Arg + Lys): 22
Atomic composition:

| | | |
|---|---|---|
| Carbon | C | 1247 |
| Hydrogen | H | 1934 |
| Nitrogen | N | 340 |
| Oxygen | O | 403 |
| Sulfur | S | 8 |

Formula: C1247H1934N340O403S8
Total number of atoms: 3932
Extinction coefficients:
Extinction coefficients are in units of M-1 cm-1, at 280 nm.
Ext. coefficient 49640
Abs 0.1% (=1 g/l) 1.748 assuming ALL Cys residues appear as half cystines
Ext. coefficient 49390
Abs 0.1% (=1 g/l) 1.739 assuming NO Cys residues appear as half cystines
Estimated half-life:
The N-terminal of the sequence considered is-Q (Gln).
The estimated half-life is: 0.8 hours (mammalian reticulocytes, in vitro).
10 min (yeast, in vivo)
10 hours (*Escherichia coli*, in vivo)
Aliphatic index: 69.21
Grand average of hydropathicity (GRAVY): −0.333

Molecular modelling of scFv 9O12.2

Pdb files of murine variable domains used as a template are:
for the VH domain: 1PLG :H; 1MNU :H; 1A5F :H; 1IGI:H.
for the VL domain: 1PLG :L; 1IGI :L; 1MNU :L; 1AXT :L.

Figure 3:
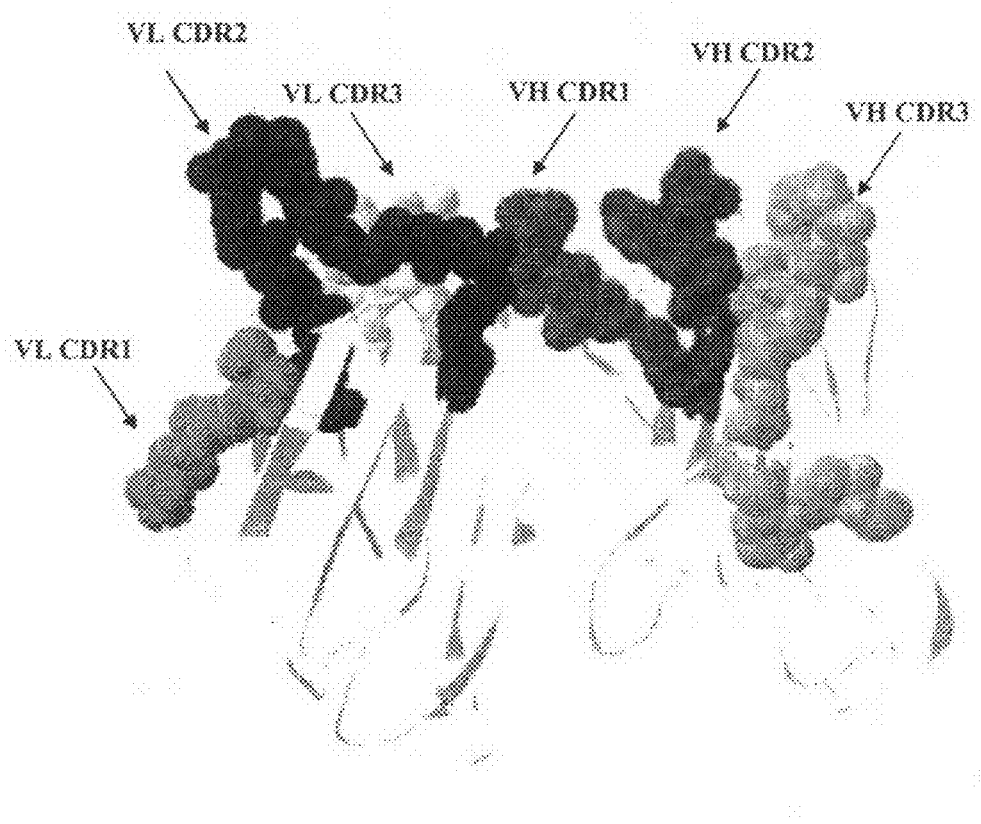
FIG. 3. Three-dimensional model of the scFv9O12.2. Model of the 9O12.2.2 antigen-binding domains (side view) The CDRs are indicated.

Modeler 3.0. software was used for the modelling of variable domains. Twenty models were designed for each domain and the best was selected according to the RMSD value: VH(RMSD: 0.13 Å); VL (RMSD: 0.703 Å). The model is shown in FIG. 3.

Analysis of the Periplasmic Extracts

Figure 4:
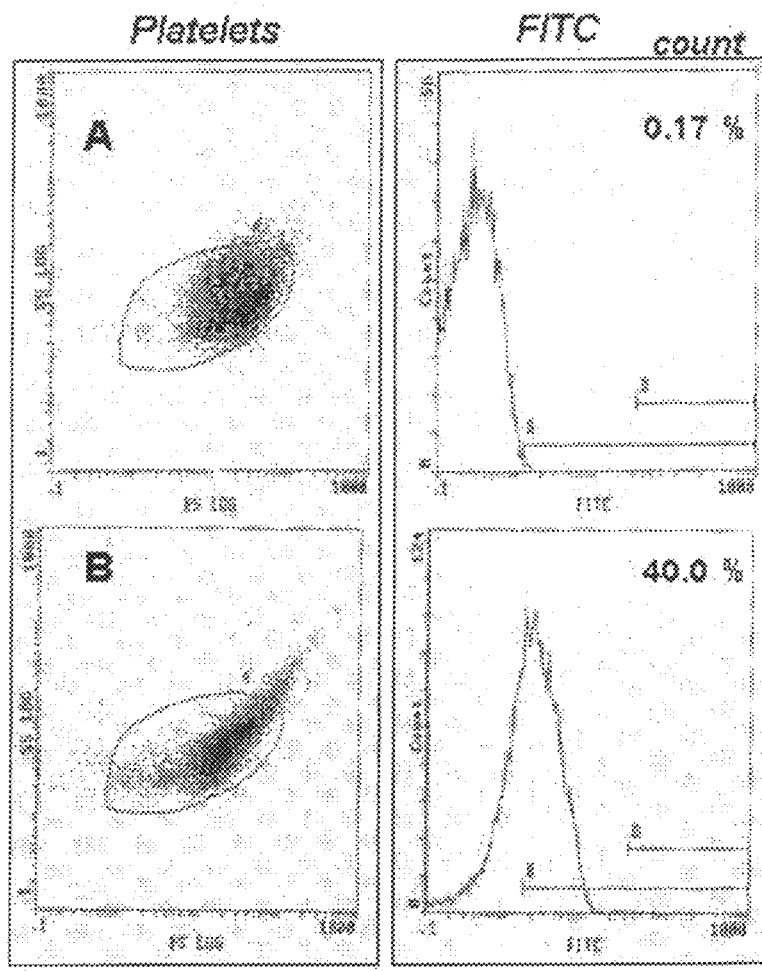
FIG. 4. Analysis of bacterial periplasmic extracts by flow cytometry on human platelets. Bacterial periplasmic extracts of induced recombinant bacteria transformed with a plasmid encoding an irrelevant scFv-myc or the plasmid pSW scFv9O12.2-myc were incubated with human platelets. Binding of scFvs was analysed using an FITC-coupled anti-cmyc antibody. A: irrelevant scFv, B: scFv 9O12.2. Left panel: forward versus side scatter; right panel: fluorescence histogram.

To assess whether the scFv had the expected anti-GPVI activity, the periplasmic extracts were tested using human platelets and an FITC-coupled anti-c-myc IgG. FIG. 4 shows a shift to the right of the platelet fluorescence in the presence of the 9O12.2 scFv (40% positive platelets) but not in the presence of the irrelevant scFv (0.17% positive platelets). Furthermore, when the periplasmic extracts were incubated with immobilised recombinant soluble GPVI only binding of the scFv 9O12.2 was detected. Together, these results indicate that the 9O12.2 scFv retains anti-GPVI properties.

Production and Purification of the 9O12.2 scFv

The proteins contained in the periplasmic extract, the flow through fraction and the fraction eluted from the GPVI-sepharose column were analysed by SDS-PAGE and by immunoblot (FIGS. 5A and 5B). The eluted fraction appears as a major band of ~28 kDa that is in agreement with the theoretical mass. This band is also detected by immunoblot using an anti-c-myc antibody. These results indicate that affinity chromatography allows obtaining a rather pure scFv fraction.

Size Exclusion Chromatography

Figure 6:
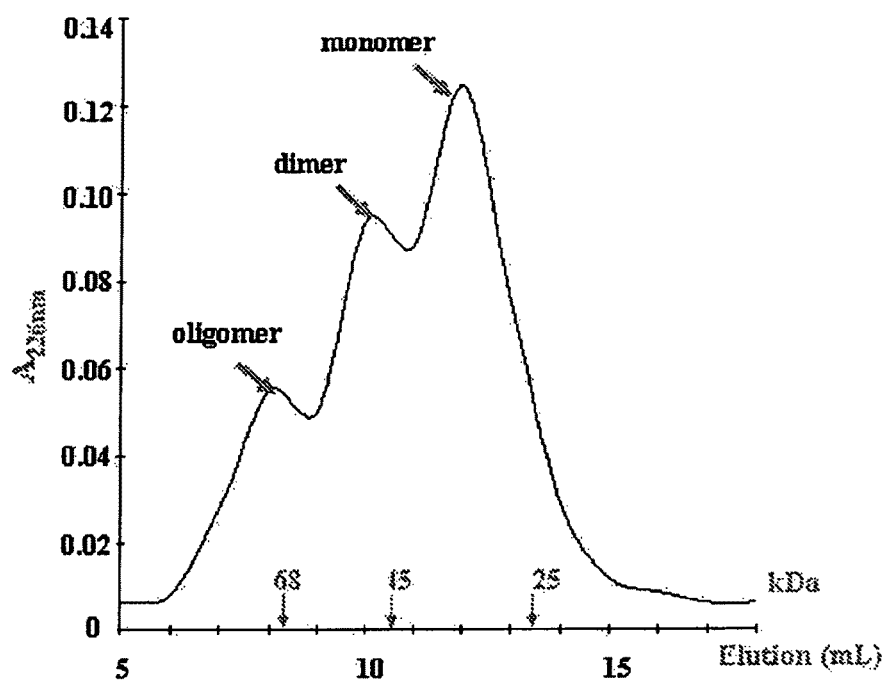
FIG. 6. Size exclusion chromatography of native scFv. The size exclusion chromatography of affinity purified scFv 9O12.2 was performed on a Superdex 75 HR 10/30 column calibrated with standards of known molecular mass.

When the purified preparation of scFv was applied on a Superdex 75 HR 10/30 column one major peak of ~25 kD corresponding to monomeric scFv was observed (FIG. 6). This peak was preceded by two less important peaks at 45 and 68 kDa corresponding to dimeric and oligomeric scFv.

The monomeric scFv was very stable, and the multimeric forms spontaneously reverted back to monomers when stored at 4° C., which is essential to preserve monovalent binding to GPVI and biological effects. Indeed, it is well-established that bivalent anti-GPVI molecules (IgGs or F(ab)'$_2$) can cause platelet activation (40; 93).

Figure 7:
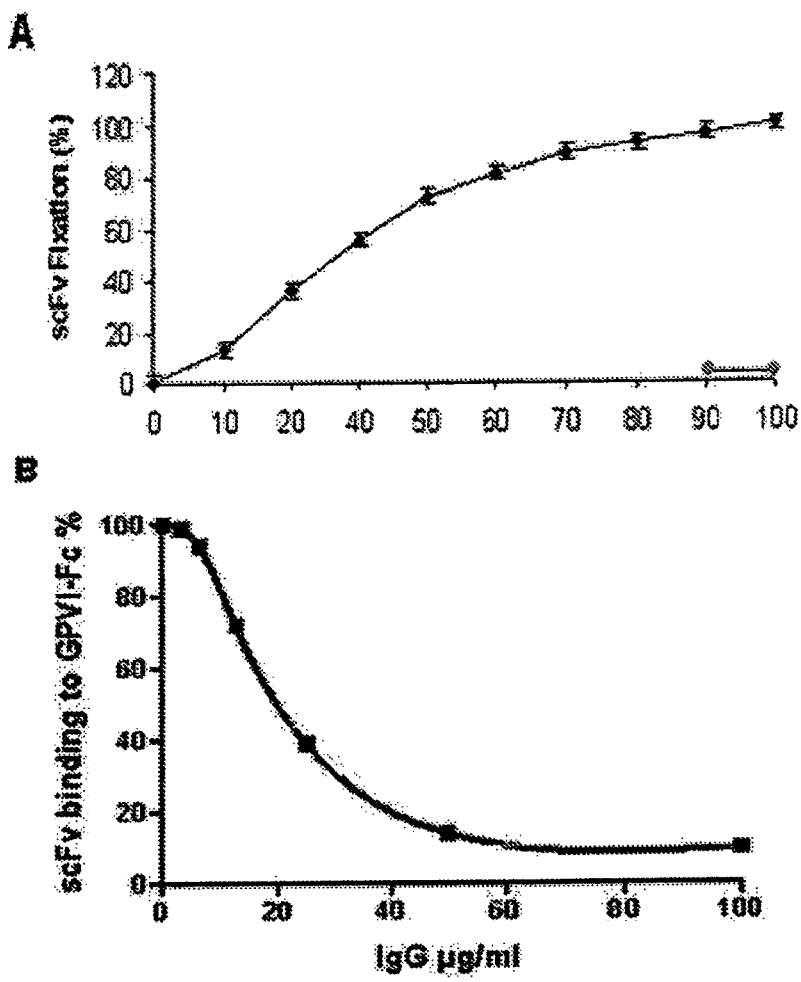
FIG. 7. Binding of purified scFv 9O12.2 to immobilized GPVI-Fc. scFv 9O12.2 (dark) or irrelevant scFv (grey symbol) was incubated on GPVI-Fc coated plates and detected using HRP coupled anti-c-myc (A): binding isotherm.

Binding of the 9O12.2 scFv to Purified GPVI-Fc and Competition with the 9O12.2 IgG The purified scFv dose dependently bound to purified GPVI-Fc immobilized on a microtitration plate (FIG. 7A). Specificity of the binding is indicated by the fact that a non relevant scFv did not bind to GPVI in the same conditions.

Furthermore binding of the scFv to purified GPVI was dose dependently inhibited by the parental IgG (FIG. 7B).

Affinity of the 9O12.2 scFv for Soluble GPVI

The affinity of the 9O12.2 IgG and of its Fab prepared after papain digestion (pFab) for GPVI-Fc determined by surface plasmon resonance are high with Kd of respectively 6.5 $10^{-9}$M and 4.5 $10^{-9}$M. The Kd of the scFv is of 2.5 $10^{-9}$M (FIG. 8).

In a second series of experiments, the following values of kinetic parameters were determined: $k_{on}$=6.5×$10^4$ $M^{-1}s^{-1}$, $k_{off}$=1.7×$10^{-1}s^-$ and the dissociation constant $K_D$=2.6 nM for the 9O12.2 scFv; and $K_D$=2.3 nM for the 9O12 proteolytic Fab fragment and $K_D$=4.0 nM for the parental IgG. These values are very similar to those obtained in the first experiments and confirm the nanomolar $K_D$ value.

Thus, the murine scFv 9O12 still has very high functional affinity, with a $K_D$ value in the range of $10^{-9}$M, and this certainly contributes to the stability of the scFv-platelet GPVI complexes, which is essential to inhibit platelet aggregation under flow conditions.

The Purified 9O12.2 scFv Inhibits GPVI Binding to Collagen.

The 9O12.2 scFv dose dependently inhibited the binding of purified GPVI-Fc to immobilized fibrillar collagen type I. (FIG. 9). Its inhibitory capacity is close to that of the 9O12.2 pFab.

More precisely, mscFv 9O12 inhibited GPVI binding to collagen with an $IC_{50}$ of approximately 1.17 µg.mL$^{-1}$ (42 µM), 80% inhibition being reached at a concentration of 5 to 10 µg.mL$^{-1}$ of $_m$scFv 9O12. This inhibitory capacity was comparable to that observed for Fab 9O12 prepared after papain digestion of the parental IgG (2.1 µg.mL$^{-1}$; 15 nM).

The purified 9O12.2 scFv binds to human platelets and inhibits collagen-induced platelet aggregation.

Binding of purified scFv to human platelets was measured by flow cytometry. A shift to the right of the peak indicates that the scFv binds to human platelets in a dose dependant manner (FIG. 10). A non relevant purified scFv did not bind to platelets.

The effect of the 9O12.2 scFv on GPVI function was tested by measuring collagen-induced platelet aggregation. For this purpose, the monomeric forms of the scFv were purified by size exclusion gel chromatography. The 9O12.2 scFv (25 µg/mL) completely prevented collagen-induced platelet aggregation (FIG. 11) as did the 9O12.2 pFab used at the same concentration.

Platelet Aggregation Under Flow Conditions

In addition, the effects of $_m$scFv 9O12 on platelet adhesion and aggregation to collagen was investigated under arterial flow conditions, and compared to those of Fab 9O12 and an irrelevant scFv (see FIG. 12). Once again, platelet aggregation induced by collagen was inhibited. In the presence of the scFv or of the Fab, only isolated platelets were observed attached to the collagen fibers in agreement with previous results (9; 41) and, in contrast to control conditions, no large platelet aggregates were observed.

Thrombin Generation

Since Fab 9O12 is known to inhibit thrombin generation at the surface of collagen-stimulated platelets, the effect of the purified $_m$scFv 9O12 was tested using the thrombogram method (FIG. 13). $_m$scFv 9O12 and Fab 9O12 reduced the thrombin peak to similar extents, and increased the lag preceding thrombin generation, indicating that $_m$scFv 9O12 is as efficient as Fab 9O12 in inhibiting collagen-induced platelet procoagulant activity.

1.2.2 First Humanized 9O12.2 scFv (hscFv 9O12.2(1))

The inventors have then humanized the murine 9O12.2 scFv fragment as described in paragraph 1.1.2. The nucleotide sequence and deduced amino acid sequence of humanized VH and VL domains and of the first humanized 9O12.2 scFv fragment (hscFv 9O12.2(1)) are displayed in FIG. 14. This hscFv 9O12.2(1) fragment was then further characterized using affinity binding to GPVI sepharose: The periplasmic fraction of recombinant bacteria was loaded onto a GPVI sepharose column. Retained proteins were analyzed by Western-Blot using an anti-c-myc IgG followed by anti-mouse antibody coupled to HRP and ECL revelation. A single band is detected with a molecular mass of 28.5 kDa (FIG. 15) as expected for the humanized scFv.

The binding of hscFv 9O12.2(1) to GPVI-Fc was then analyzed and compared to that of murine scFv 9O12.2 (mscFv 9O12.2). Purified humanized scFv and mscFv were injected on GPVI-Fc immobilized on a CM5 sensorchip. Results are displayed on FIG. 16 and show that hscFv 9O12.2 (1) also binds to GPVI-Fc, with what appears to be a higher affinity than mscFv.

Finally, the binding of hscFv9O12.2(1) to human platelets was studied. Human platelets were incubated with bacterial periplasmic extracts. hscFv 9O12.2(1) bound to platelets was detected using FITC coupled anti-c-myc antibody. Binding to platelet were analyzed on XL Epics Coulter Flow cytometer. An irrelevant scFv was used as a negative control. Results are displayed in FIG. 17 and show a shift to the right of the histogram for hscFv, which indicates that the humanized hscFv 9O12.2(1) binds to platelet GPVI.

1.3 Conclusion

The results displayed above clearly show that despite essential structural modifications, the murine 9O12.2 scFv generated by the inventors from the 9O12.2 monoclonal antibody specifically binds to human GPVI with a high affinity. In addition, it inhibits GPVI binding to collagen and prevents collagen-induced platelet aggregation, thus inhibiting GPVI function.

This scFv fragment thus displays all the advantages of scFv fragments while retaining the affinity and inhibition capacity of corresponding Fab fragments.

In addition, the inventors have also generated a first humanized version of the 9O12.2 scFv fragment, which also binds to human GPVI with a high affinity despite new essential structural modifications (hscFv 9O12.2(1)).

This first humanized 9O12.2 scFv fragment (hscFv 9O12.2) further has the advantage of a potentially minimally reduced immunogenicity.

This application thus describes for the first time a low molecular weight, low immunogenic GPVI ligand with a high capacity to inhibit platelet aggregation, resulting in a very promising product for arterial thrombosis treatment.

Example 2

Synthesis and Activity of a Second Optimized Humanized Single Chain Variable Fragment hscFv 9O12.2(2) Directed Against Human Glycoprotein VI Production of the recombinant first humanized hscFv 9O12.(1) fragment was difficult, and so some refinements in the construct were called for. A second optimized humanized hscFv 9O12.(2) fragment was thus derived from hscFv 9O12. (1).

2.1 Experimental Procedure

Construction of the Second Humanized scFv Fragment (hscFv 9O12.2(2))

We postulated that unforseen structural incompatibilities between the original murine CDRs and the human acceptor frameworks could have led to misfolding of the V-domains, and to the formation of insoluble inclusion bodies that remained sequestered in the bacterial cytoplasm. To get round these difficulties, some minor refinements were undertaken.

First, we observed that 9O12 CDR L1 loop is 5 residues longer than that of 1VGE, and that 9O12 and 1VGE frameworks 1 and 2 have a low identity score (48% and 73% respectively) (FIG. 19). This suggested that the 1 VGE light chain FR1 and FR2 are not suitable for the correct folding of CDR L1.

Extra FASTA searches were then performed using 9O12 VL FR1 and FR2. An excellent match was found with human 1×9Q for FR1 and FR2 (95.6 and 86.6 identity scores respectively, and 100% similarities in both cases). In addition, loop L1 (CDR1) of the selected antibody 1×9Q was similar in length to that of 9O12.

We therefore decided to preserve the original murine 9O12 VL FR1 and FR2 in the novel humanized hscFv 9O12.(2) construction, since the sequences of these frameworks fit well with another human antibody framework (1×9Q), the CDR L1 of which is exactly the same size as that of 9O12 (see FIG. 19).

Other refinements were carried out on the basis of close inspection of the model. Indeed, we also retained in the final $_h$scFv 9O12 construct a very limited number of residues that could influence the ability of CDR loops to adopt their conformation. Two critical areas were preserved. The first one was the dipeptide LD at position 59-60 in VL. L59 (P in the human template), considered as potentially significant, since it is in the close vicinity of the residues of L CDR2. Although L and P are both hydrophobic, P has a cyclical side chain and is known to induce specific effects on the protein backbone structure (MacArthur and Thornton, 1999). In addition, we noticed that L occurs much less often than P at this position (2%), and this may be indicative of a specific role (Honegger & Pluckthun, 2001). The other unmutated murine residues with no similarities to the human template (1VGE) were located in VH FR3 ($A_{H71}$, $K_{H73}$, $R_{H76}$, Kabbat numbering). Finally, only 5 murine residues in VL and 10 in VH were maintained in the human frameworks selected for humanization.

The final construct is shown in FIG. 19. All the humanized hscFv 9O12.(2) frameworks exhibit 100% similarity with human frameworks, apart from the VH and VL Frameworks 3 (90.62 and 93.75% respectively) (see following Table 1).

TABLE 1

Identity and similarity scores of the 9O12 humanized V-domain frameworks with human antibodies frameworks used as template. x is the number of residues in the humanized FR that are identical to residues from human FR. y is the total number of residues in the FR.

| Frameworks | Identity | | Similarities |
|---|---|---|---|
| (FR) | x/y | % | % |
| $V_H$ FR1 | 23/26 | 88.46 | 100 |
| $V_H$ FR2 | 14/14 | 100 | 100 |
| $V_H$ FR3 | 25/32 | 78.12 | 90.62 |
| $V_H$ FR4 | 11/11 | 100 | 100 |
| $V_L$ FR1 | 22/23 | 95.65 | 100 |
| $V_L$ FR2 | 13/15 | 86.60 | 100 |
| $V_L$ FR3 | 30/32 | 93.75 | 93.75 |
| $V_L$ FR4 | 10/10 | 100 | 100 |

Globally, the 11 N-terminal residues from the murine VH FR3 were preserved in the final construct, because they are clearly located close to the flat part of the pocket in which the antigen is expected, and so could interact with it. Nevertheless, VH FR3 exhibits 25/32 residues identity with 1VGE. Only 3 residues of this framework ($A_{H71}$, $K_{H73}$, $R_{H76}$, Kabbat numbering) had no similarity with 1 VGE. The 9O12 VL FR3 was substituted for its 1VGE counterpart with the exception of two residues (L59P and D60S), essentially because L is not frequently encountered at this position, and D is an acidic residue.

Other Experimental Procedures

All other experimental procedures for characterizing the second hscFv 9O12.(2) fragment were performed as described in Example 1.

2.2 Results

The production of hscFv9O12.2(2) was better than that of hscFv9O12.2(1).

In addition, the purified hscFv9O12.2(2) fragment conserved high affinity for its target, as demonstrated by SPR analysis against immobilized GPVI ($k_{on}$=5.8×10$^4$ M$^{-1}$s$^{-1}$, $k_{off}$=1.86×10$^{-4}$ s$^{-1}$ and dissociation constant $K_D$=3.2 nM).

It was also able to bind to freshly prepared human platelets in flow cytometry, and the shift to the right of the fluorescence peak was always similar to that of cells labeled with the murine mscFv9O12 under similar experimental conditions (see FIG. 20B). Near-total inhibition of hscFv9O12.2(2) binding was observed when platelets were pre-mixed with an excess of Fab 9O12. These results demonstrated that the affinity-purified hscFv9O12.2(2) molecule retained the binding activity, affinity and specificity of the parent antibody for GPVI as well as for native GPVI exposed at the surface of human platelets.

2.3 Conclusion

As for hscFv9O12.2(1), the main parameters that are usually affected by humanization were well-preserved in hscFv9O12.2(2). Affinity-purified hscFv9O12.2(2) was fully functional, and had a high affinity for GPVI, a major point for biological applications. FACS analysis also indicated that hscFv9O12.2(2) recognizes the same epitope on human platelets as mouse Fab 9O12, because its binding was specifically blocked in the presence of a molar excess of Fab 9O12.

BIBLIOGRAPHY

1. WO 01/00810
2. WO 03/008454
3. Massberg S, Konrad I, Bultmann A, Schulz C, Munch G, Peluso M, Lorenz M, Schneider S, Besta F, Muller I, Hu B, Langer H, Kremmer E, Rudelius M, Heinzmann U, Ungerer M, Gawaz M. Soluble glycoprotein VI dimer inhibits platelet adhesion and aggregation to the injured vessel wall in vivo. Faseb J. 2004; 18:397-399
4. Gruner S, Prostredna M, Koch M, Miura Y, Schulte V, Jung S M, Moroi M, Nieswandt B. Relative antithrombotic effect of soluble GPVI dimer compared with anti-GPVI antibodies in mice. Blood. 2005; 105:1492-1499
5. EP 1224942
6. EP 1228768
7. EP1538165
8. WO 2005/111083
9. Lecut C, Feeney L A, Kingsbury G, Hopkins J, Lanza F, Gachet C, Villeval J L, Jandrot-Perrus M. Human platelet glycoprotein VI function is antagonized by monoclonal antibody-derived Fab fragments. J Thromb Haemost. 2003; 1:2653-2662
10. Nieswandt B, Schulte V, Bergmeier W, Mokhtari-Nejad R, Rackebrandt K, Cazenave J P, Ohlmann P, Gachet C, Zirngibl H. Long-term antithrombotic protection by in vivo depletion of platelet glycoprotein VI in mice. J Exp Med. 2001; 193:459-469.
11. Qian M D, Villeval J L, Xiong X, Jandrot-Perrus M, Nagashima K, Tonra J, McDonald K, Goodearl A, Gill D. Anti GPVI human antibodies neutralizing collagen-induced platelet aggregation isolated from a combinatorial phage display library. Hum Antibodies. 2002; 11:97-105.
12. Siljander P R, Munnix I C, Smethurst P A, Deckmyn H, Lindhout T, Ouwehand W H, Farndale R W, Heemskerk J W. Platelet receptor interplay regulates collagen-induced thrombus formation in flowing human blood. Blood. 2004; 103:1333-1341.
13. Matsumoto Y, Takizawa H, Gong X, Le S, Lockyer S, Okuyama K, Tanaka M, Yoshitake M, Tandon N N, Kambayashi J. Highly potent anti-human GPVI monoclonal antibodies derived from GPVI knockout mouse immunization. Thromb Res. 2006.
14. Juste M, Muzard J, P. Billiald. Cloning of the antibody kappa light chain V-gene from murine hybridomas by bypassing the aberrant MOPC21-derived transcript. Anal Biochem. 2006 1; 349(1):159-61
15. Kabat E. A., WU T. T., Perry H. M., Gottesman K. S., Foeller C (1991) Sequences of proteins of immunological interest. 5th edition, Public Health service, N.I.H., Washington D.C.

16. Chothia and Lesk. Canonical structures for the hypervariable regions of immunoglobulins (1987) J Mol. Biol. 1987 Aug. 20; 196(4):901-17.
17. Tsurushita N, Hinton P R & Kumar S (2005) Design of humanized antibodies: from anti-Tac to Zenapax. *Methods* 36, 69-83
18. Fontayne A, Vanhoorelbeke K, Pareyn I, Van Rompaey I, Meiring M, Lamprecht S, Roodt J, Desmet J & Deckmyn H (2006) Rational humanization of the powerful antithrombotic anti-GPIbalpha antibody: 6B4. *Thromb Haemost.* 96, 671-84.
19. Lazar G A, Desjarlais J R, Jacinto J, Karki S & Hammond P W (2007) A molecular immunology approach to antibody humanization and functional optimization. *Mol. Immunol.* 44, 1986-1998.
20. Jones P T, Dear P H, Foote J, Neuberger M S, Winter G. "Replacing the complementarity-determining regions in a human antibody with those from a mouse". Nature. 1986; 321:522-525
21. Verhoeyen M, Milstein C, Winter G. Reshaping human antibodies: grafting an antilysozyme activity. Science. 1988; 239:1534-1536
22. Caldas C, Coelho V, Kalil J, Moro A M, Maranhão A Q & Brígido M M (2003) Humanization of the anti-CD18 antibody 6.7: an unexpected effect of a framework residue in binding to antigen. *Mol. Immunol.* 39, 941-52
23. Gonzales N R, Padlan E, De Pascalis R, Schuck P, Schlom J & Kashmiri S V (2004) SDR grafting of a murine antibody using multiple human germline templates to minimize its immunogenicity. *Mol Immunol.* 41, 863-872.
24. WO98/45322;
25. WO 87/02671;
26. U.S. Pat. No. 5,859,205;
27. U.S. Pat. No. 5,585,089;
28. U.S. Pat. No. 4,816,567;
29. EP0173494
30. Riechmann L, Clark M, Waldmann H, Winter G. Reshaping human antibodies for therapy. Nature. 1988; 332:323-327
31. Winter G & Milstein C. Man-made antibodies. Nature. 1991 Jan. 24; 349(6307):293-9.
32. Ewert S, Honegger A, Pluckthun A. Stability improvement of antibodies for extracellular and intracellular applications: CDR grafting to stable frameworks and structure-based framework engineering. Methods. 2004; 34(2):184-99.
33. EP1297172
34. EP1522590
35. Hamilton S R et al. Production of complex human glycoproteins in yeast. Science. 2003 Aug. 29; 301(5637):1244-6.
36. Wildt S and Gerngross T U. The humanization of N-glycosylation pathways in yeast. Nat Rev Microbiol. 2005 February; 3(2):119-28.
37. Ward E S, Gussow D, Griffiths A D, Jones P T, Winter G. Binding activities of a repertoire of single immunoglobulin variable domains secreted from *Escherichia coli*. Nature 1989; 341: 544-546.
38. Lecut C, Feijge M A, Cosemans J M, Jandrot-Perrus M & Heemskerk J W (2005) Fibrillar type 1 collagens enhance platelet-dependent thrombin generation via glycoprotein VI with direct support of alpha2beta1 but not alphaIIbbeta3 integrin. *Thromb Haemost.* 94, 107-114.
39. Hemker H C, Giesen P L, Ramjee M, Wagenvoord R & Béguin S (2000) The thrombogram: monitoring thrombin generation in platelet-rich plasma. *Thromb Haemost.* 83, 589-591.
40. Sugiyama T, Okuma M, Ushikubi F, Sensaki S, Kanaji K & Uchino H (1987) A novel platelet aggregating factor found in a patient with defective collagen-induced platelet aggregation and autoimmune thrombocytopenia. Blood 69, 1712-1720.
41. Lecut C, Schoolmeester A, Kuijpers M J, Broers J L, van Zandvoort M A, Vanhoorelbeke K, Deckmyn H, Jandrot-Perrus M & Heemskerk J W (2004) Principal role of glycoprotein VI in alpha2beta1 and alphaIIbbeta3 activation during collagen-induced thrombus formation. *Arterioscler Thromb Vasc Biol.* 24, 1727-33.

The invention claimed is:

1. A humanized single chain scFv antibody directed against human glycoprotein VI, comprising or consisting of SEQ ID NO:28 or SEQ ID NO:47.

2. The humanized single chain scFv antibody of claim 1, as a medicament.

3. A pharmaceutical composition, comprising the humanized single chain scFv antibody of claim 1 and a pharmaceutically acceptable carrier.

4. A method for inhibiting platelet aggregation induced by collagen or treating thrombosis comprising administering to a subject in need thereof the humanized single chain scFv antibody of claim 1.

5. An isolated nucleic acid encoding the humanized single chain scFv antibody of claim 1.

6. An isolated nucleic acid comprising or consisting of SEQ ID NO:29.

7. An isolated nucleic acid comprising or consisting of SEQ ID NO:30 or SEQ ID NO:49.

8. An expression vector comprising the isolated nucleic acid of claim 5.

9. An isolated host cell comprising the expression vector of claim 8.

10. A method for preparing the humanized single chain scFv antibody of claim 1, comprising:

a) Culturing the host cell of claim 9, and b) Purifying the humanized single chain scFv antibody.

* * * * *